(12) United States Patent
Foody et al.

(10) Patent No.: US 8,003,352 B2
(45) Date of Patent: Aug. 23, 2011

(54) METHOD OF OBTAINING A PRODUCT SUGAR STREAM FROM CELLULOSIC BIOMASS

(75) Inventors: Brian Foody, Ontario (CA); Jeffrey S. Tolan, Ontario (CA)

(73) Assignee: Iogen Energy Corporation, Ontario (CA)

( * ) Notice: Subject to any disclaimer, the term of this patent is extended or adjusted under 35 U.S.C. 154(b) by 1236 days.

(21) Appl. No.: 11/658,338

(22) PCT Filed: Jul. 15, 2005

(86) PCT No.: PCT/CA2005/001098
§ 371 (c)(1),
(2), (4) Date: Jan. 24, 2007

(87) PCT Pub. No.: WO2006/007691
PCT Pub. Date: Jan. 26, 2006

(65) Prior Publication Data
US 2009/0023187 A1    Jan. 22, 2009

Related U.S. Application Data

(60) Provisional application No. 60/588,661, filed on Jul. 16, 2004.

(51) Int. Cl.
*C12P 19/00* (2006.01)
(52) U.S. Cl. ........... 435/72; 435/209; 536/127; 536/128
(58) Field of Classification Search ............ 435/72, 435/209; 536/127, 128
See application file for complete search history.

(56) References Cited

U.S. PATENT DOCUMENTS

| | | | |
|---|---|---|---|
| 4,101,338 A | 7/1978 | Rapaport et al. | |
| 4,237,226 A | 12/1980 | Grethlein | |
| 4,359,430 A | 11/1982 | Heikkila et al. | |
| 4,461,648 A | 7/1984 | Foody | |
| 4,631,129 A | 12/1986 | Heikkila | |
| 5,407,580 A | 4/1995 | Hester et al. | |
| 5,536,325 A | 7/1996 | Brink | |
| 5,560,827 A | 10/1996 | Hester et al. | |
| 5,580,389 A | 12/1996 | Farone et al. | |
| 5,628,907 A | 5/1997 | Hester et al. | |
| 5,789,210 A | 8/1998 | Ho et al. | |
| 5,820,687 A | 10/1998 | Farone et al. | |
| 5,968,362 A | 10/1999 | Russo, Jr. | |
| 6,482,268 B2 | 11/2002 | Hyoky et al. | |
| 6,663,780 B2 | 12/2003 | Heikkila et al. | |
| 6,709,527 B1 | 3/2004 | Fechter et al. | |
| 7,585,652 B2 * | 9/2009 | Foody et al. | 435/163 |

FOREIGN PATENT DOCUMENTS

| | | |
|---|---|---|
| EP | 1306442 | 5/2005 |
| GB | 1 483 327 | 8/1977 |
| WO | WO 95/17517 | 6/1995 |
| WO | WO 2006007691 A1 * | 1/2006 |

OTHER PUBLICATIONS

Nilvebrant, et al, "Detoxification of Lignocellulose Hydrolysates with Ion-Exchange Resins", Applied Biochemistry and Biotechnology, vol. 91-93 (2001), pp. 35-49.

Wooley, et al., "A Nine-Zone Simulating Moving Bed for the Recovery of Glucose and Xylose from Biomass Hydrolyzate", Ind. Eng. Chem. Res., vol. 37, No. 9 (1998), pp. 3699-3709.

Bipp, et al., "Application of ion exclusion chromatography (IEC) for the determination of sugar and . . . ", Fresenius J Anal Chem, vol. 357 (1997), pp. 321-325.

\* cited by examiner

*Primary Examiner* — Sandra Saucier
*Assistant Examiner* — Susan Hanley
(74) *Attorney, Agent, or Firm* — Fitzpatrick, Cella, Harper & Scinto

(57) ABSTRACT

The invention relates to a process for obtaining a product sugar stream from a cellulosic biomass, comprising pretreating the cellulosic biomass to hydrolyze a portion of the cellulose and hemicellulose to produce glucose, acetic acid and a sugar monomer, adding base to the pretreated cellulosic biomass to produce inorganic salt and acetate salt; hydrolyzing the neutralized cellulosic biomass with cellulase enzymes and separating insoluble residue from the resulting sugar stream; treating the clarified sugar stream using exclusion chromatography at a pH of 5 to 10 to produce a product sugar stream.

48 Claims, 7 Drawing Sheets

METHOD OF OBTAINING A PRODUCT SUGAR STREAM FROM CELLULOSIC BIOMASS

This application is a 371 of PCT application No. PCT/CA2005/001098 filed Jul. 15, 2005, which claims benefit of U.S. Provisional Patent Application No. 60/588,661 filed Jul. 16, 2004.

The present invention relates to a method of obtaining a product sugar stream from cellulosic biomass, more particularly to a method of obtaining a product sugar stream produced from the enzymatic conversion of cellulosic biomass to sugar.

BACKGROUND OF THE INVENTION

Fuel ethanol is currently produced from feedstocks such as cornstarch, sugar cane, and sugar beets. However, the production of ethanol from these sources cannot expand much further due to limited farmland suitable for the production of such crops and competing interests with the human and animal food chain. Finally, the use of fossil fuels, with the associated release of carbon dioxide and other products in the conversion process, is a negative environmental impact of the use of these feedstocks The possibility of producing fuel ethanol from, cellulose-containing feedstocks, such as agricultural wastes, grasses, forestry wastes, and sugar processing residues has received much attention due to the availability of large amounts of these inexpensive feedstocks, the desirability to avoid burning or landfilling cellulosic waste materials, and the cleanliness of ethanol as a fuel compared to gasoline. In addition, a byproduct of the cellulose conversion process, lignin, can be used as a fuel to power the cellulose conversion process, thereby avoiding the use of fossil fuels. Studies have shown that, taking the entire cycle into account, the use of ethanol produced from cellulose generates close to nil greenhouse gases.

The cellulosic feedstocks that may be used for ethanol production include (1) agricultural wastes such as corn stover, wheat straw, barley straw, canola straw, and soybean stover; (2) grasses such as switch grass, miscanthus, cord grassland reed canary grass; (3) forestry wastes such as aspen wood and sawdust; and (4) sugar processing residues such as bagasse and beet pulp.

Cellulose consists of a crystalline structure that is very resistant to breakdown, as is hemicellulose, the second most prevalent component. The conversion of cellulosic fibers to ethanol requires: 1) liberating cellulose and hemicellulose from lignin or increasing the accessibility of cellulose, and hemicellulose within the cellulosic feedstock to cellulase enzymes; 2) depolymerizing hemicellulose and cellulose carbohydrate polymers to free sugars; and 3) fermenting the mixed hexose and pentose sugars to ethanol.

The feedstock is conveyed into the plant and the feedstock particles are typically reduced to the desired size to be suitable for handling in the subsequent processing steps.

Among well-known methods used to convert cellulose to sugars is an acid hydrolysis process involving the use of steam and acid at a temperature, acid concentration and length of time sufficient to hydrolyze the cellulose to glucose (Grethlein, *J. Appl. Chem. Biotechnol.,* 1978, 28:296-308). The glucose is then fermented to ethanol using yeast, and the ethanol is recovered and purified by distillation. Acid hydrolysis has been studied for many years and has not been a commercial success due to low sugar yields at the harsh hydrolysis conditions.

An alternative method of cellulose hydrolysis is an acid prehydrolysis (or pre-treatment) followed by enzymatic hydrolysis. In this sequence, the cellulosic material is first pretreated in a process that is analogous to the acid hydrolysis process described above, but using milder temperatures, lower acid concentrations, shorter treatment time, or a combination of these. This pretreatment process increases the accessibility of cellulose within the cellulosic fibers for subsequent conversion steps, but results in little conversion itself. In the next step, the pretreated feedstock is adjusted to an appropriate temperature and pH, typically 50° C., pH 5, and then submitted to enzymatic conversion by cellulase enzymes. The steam temperature, sulfuric acid concentration, and treatment time in a pretreatment process are chosen to be significantly milder than that in the acid hydrolysis process, such that the exposed cellulose surface area is greatly increased as the fibrous feedstock is converted, to a muddy texture. Much of the hemicellulose is hydrolyzed, but there is little conversion of the cellulose to glucose. The cellulose is hydrolyzed to glucose in a subsequent step that uses cellulase enzymes, and the steam/acid treatment in this case is known as pretreatment.

The hydrolysis of the cellulose, whether by acid or by cellulase enzymes, is followed by the fermentation of the sugar to ethanol, which is then recovered by distillation.

The efficient conversion of cellulose from cellulosic material into sugars and the subsequent fermentation of sugars to ethanol represent a major challenge to the industry. In particular, a large amount of impurities, including salt, sugar degradation products, organic acids, soluble phenolic compounds, and other compounds are present in the sugar stream after the pretreatment. These compounds result from degradation of the feedstock or, in the case of the salts, from the acids and alkali added in the process. The presence of these impurities is highly inhibitory to the fermentation of the sugar by the yeast. In the absence of art efficient fermentation of the sugar in high; yield, the production of ethanol from biomass is not commercially viable. Furthermore, the inability to recover acetic acid and salt from the sugar streams, due to the large amount of impurities present, represents a loss of potential revenue in the process.

The removal of toxic inhibitors, sulfuric acid and sulfate salts, and acetic acid and acetate salts from the sugar streams prior to fermentation has been the subject of a significant amount of research. The processes studied include lime addition, ion exchange, and ion exclusion.

In lime addition, lime (calcium hydroxide), which is insoluble, is added to the sugar stream to precipitate impurities. The limed sugar solution has an alkaline pH and is neutralized with acid, typically phosphoric acid, sulfurous acid, carbonic acid, or a mixture thereof. Optionally, the lime cake is separated from the sugar by filtration. A second option is to filter the lime cake at alkaline pH and carry out a second filtration to remove material that precipitates during the acidification steps. Lime treatment decreases the toxicity of the sugar stream to yeast and other microbes. However, any handling of the lime cake is difficult and costly. In addition, the introduction of calcium into the stream increases the likelihood that calcium scale will deposit on evaporators, distillation columns, and other process equipment. The clean-up and avoidance of scale increases the cost of sugar processing. Furthermore, the introduction of lime makes the recovery of salt and acetic acid more difficult.

In ion exchange, the sugar stream is flowed through columns packed with ion exchange resins. The resins are in a cation exchange or anion exchange form, or a combination of the two. In principle, cation-exchange resins remove cations such as sodium or potassium, while anion-exchange resins remove anions such as sulfate and acetate. For example, ion exchange has been investigated by Nilvebrant et al. (*App. Biochem. Biotech.*, 2001, 91-93:35-49) in which a spruce hydrolyzate was treated to remove fermentation inhibitors, such as phenolic compounds, furan aldehydes and aliphatic acids. The separation was carried out using an anion exchanger, a cation exchanger and a resin without charged groups. The investigators found mat treatment at pH 10.0 using an anionic exchanger removed phenolic inhibitors since at this pH most of the phenolic groups were ionized.

In practice, several factors limit the effectiveness of ion exchange treatment to remove inhibitors. First, the multi-component nature of the streams results in an inefficient removal of some species, at any single set of conditions. Second, the high ionic load demands very frequent and expensive regeneration of the resin. Finally, not all of the inhibitors are ionic, and ion exchange is ineffective in removing nonionic compounds from sugar.

Ion exclusion uses ion exchange resins, but rather than bind target ions in solution, the charge on the resin matches that of the target ions in the solution, thereby excluding them from the resin. The excluded compounds then elute from the column readily, while uncharged compounds absorb into the resin and elute from the column more slowly. For example, a concentrated solution of sulfuric acid and glucose has hydrogen as the primary cation. A cation-exchange resin in the hydrogen form will exclude the acid, causing it to elute quickly. The glucose, which is uncharged, is not excluded from the resin and absorbs into the resin void, thereby eluting from the column more slowly than the acid.

Ion exclusion for detoxification of sugars from biomass streams has been described by various groups. For example, Wooley et al., (*Ind. Eng. Chem. Res.*, 1998, 37:3699-3709) teaches the removal of acetic acid and sulfuric acid from biomass sugars by pumping a product stream over, a bed of cation exchange resin in the hydrogen form. The positive charge on the resin repels the hydrogen ion in the sulfuric acid, thereby causing the sulfuric acid to elute from the column very quickly. The uncharged sugar molecules are absorbed into the void space of the resin and elute from the column more slowly than the sulfuric acid. Fully associated acetic acid (non-ionic) is a smaller molecule than sugar or sulfuric acid and so elutes from the column more slowly than sulfuric acid or sugar. Also described is a Simulated Moving Bed (SMB) system for producing a glucose stream free of sulfuric acid and acetic acid. A shortcoming of Wooley's process is that the glucose recovery is only 92%. The 8% loss of glucose represents a significant cost in the system. The ion exclusion was carried out at a pH of between about 1-2 and, at such low pH values, significant degradation of xylose is likely.

U.S. Pat. Nos. 5,560,827 and 5,628,907 (Hester et al.) disclose a process for separating an ionic component (acid) from a non-ionic component (sugar) using an SMB arrangement, including a plurality of ion exclusion columns arranged in 4 zones. The separations are run at a low pH using a cationic (or cation-exchange) resin in the hydrogen form. The methods of Hester incorporate various arrangements to minimize the dispersion and channeling effects. The sugar/acid solution is loaded onto the column and the acid elutes first while sugar is eluted later using water.

U.S. Pat. No. 5,407,580 (Hester et al.) discloses a process for separating an ionic component (acid) from a non-ionic component (sugar) using a preparative-scale ion exclusion system. The system includes a floating head distribution plate to prevent evolution of a dilution layer caused by the shrinkage of the resin bed. The columns can be operated over a range of process conditions to produce separate and distinct elution profiles for the acid and sugar. Acceptable conditions for carrying out the process are at a sulphuric acid concentration of 1.0 to 20.0%, a feed volume of 1.0 to 5.0, a flux rate of 0.1 to 2.0 and using a divinylbenzene resin with a percent crosslinking of between 1.0 and 15.

U.S. Pat. Nos. 5,580,389 and 5,820,687 (Farone et al.) teach a method of producing and separating sugars. The two-step method involves decrystallizing and hydrolyzing biomass using acid, then pressing the hydrolyzate and collecting the liquid, which contains acid and sugars. The liquid is loaded onto a cross-linked strong cation exchange resin run at low pH, where the sugars adsorb to the resin. The resin is purged with gas, pushing the acid out of the resin; the resin is then washed with water, producing a sugar stream.

U.S. Pat. No. 5,968,362 (Russo et al.) discloses a method of separating sugars and acid by ion exclusion chromatography using an anion exchange resin. The sugars elute through the column, and may contain residual acid and heavy metals. The heavy metals, can be removed and the acid neutralized using a lime treatment. The acid adsorbs to the resin and is retained; it is eluted from the resin with water.

Nanguneri et al. (*Sep. Sci. Tech.*, 1990, 25(13-15):1829-1842) simulated the separation of sugars from acids using a modified mathematical model and compared the results obtained with experimental data. Separation performances at different process parameters were then analyzed to determine optimal processing conditions. The simulated process would result in an acid-rich stream eluting first, followed by a dilute acid/sugar interface stream and then a sugar-rich stream. Nanguneri et al. performed an economic analysis at the optimal processing conditions and concluded that ion exclusion is highly feasible for the processing of lignocellulosic feedstocks to produce ethanol. However, a drawback of the method of Nanguneri et al. is that the dilute acid/sugar interface stream is costly to separate and recover.

U.S. Pat. No. 6,663,780 (Heikkilä et al.) discloses a method in which product tractions, such as sucrose, betaine and xylose, are separated from molasses that are obtained from a variety of sources, including beet and cane molasses, as well as hydrolyzates produced from biomass. The process involves treating the molasses with sodium carbonate (pH 9) to precipitate calcium followed by removing the resulting precipitate. The filtrate is then subjected to a simulated moving bed (SMB); process which is carried out using at least two SMB systems packed with a strongly acid cation exchange resin. Sucrose is recovered in a first system and betaine is recovered in a second system. The sucrose obtained from the first system may be crystallized and the crystallization run-off applied to the second system. Also, described is a process for recovering xylose from sulphite cooking liquor using two systems. Prior to fractionation in the first system, the sulphite cooking liquor, having a pH of 3.5, is filtered and diluted to a concentration of 47% (w/w). The xylose fractions obtained from the first system are crystallized and, after adjustment to pH 3.6 with MgO, the run-off is fed to the second system. In the second system, a sequential SMB is used to separate xylose from the crystallization run-off.

A disadvantage of the separation technique disclosed in U.S. Pat. No. 6,663,780 (Heikkilä et al.) is that the inclusion of two SMB systems is costly and adds to the complexity of the process. In addition, sugars present in a hydrolyzate produced by the processing of lignocellulosic biomass are much more difficult to crystallize than sucrose in a beet process. The initial sucrose purification by crystallization in U.S. Pat. No. 6,663,780 is not successful with glucose in biomass systems.

Various groups have reported the separation of sucrose from molasses obtained from sugar carte using ion exclusion chromatography or ion exchange. For example, U.S. Pat. No. 4,359,430 (Heikkilä et al.) discloses a method of recovering betaine from inverted molasses. The molasses are first diluted with water to a concentration of 35-40% and then applied to a column containing a cation exchange resin. On elution with water, a first non-sugar waste fraction is obtained, followed by a second sugar-containing fraction, and a third fraction containing betaine. The betaine is recovered by evaporation and crystallization. Although high levels of betaine are recovered, the patent, does not address the recovery of sucrose from the sugar-containing fraction.

U.S. Pat. No. 6,482,268 (Hyöky et al.) also discloses a method of separating sucrose and betaine from beet molasses by a simulated moving bed (SMB) process. Similar to U.S. Pat. No. 6,663,780, the method of Hyöky et al. involves first precipitating calcium from the beet molasses by adding sodium carbonate and filtering the resulting calcium carbonate by filtration. The beet molasses are next applied to a column packed with a strong cation exchanger resin with a divinylbenzene backbone. A sucrose fraction is eluted first, followed by a betaine fraction, which is then concentrated and further fractionated to yield a second sucrose fraction and a second betaine fraction containing some sucrose. The second sucrose and betaine fractions are combined with the sucrose and betaine fractions obtained from the initial fractionation. Although Hyöky et al. describe the separation of sucrose and betaine from beet molasses, in a biomass conversion process these components would not be present.

A method of separating sugar from molasses using ion exclusion chromatography is taught in GB 1,483,327 (Munir et al.). The ion exclusion column comprises two types of cation exchange, resins used in the salt form to help prevent shrinkage of the column bed. Sugar adsorbs to the column and is eluted using decarbonized water adjusted to a pH of greater than 9.

WO 95/17517 (Chieffalo et al.) discloses a method of processing municipal solid waste to recover reusable materials and to make ethanol. Cellulosic material is shredded and pre-treated with acid and lime to remove heavy metals, then treated with concentrated acid (sulfuric) to produce sugars. The sugars and the acid are separated on a strong acidic cation ion exchange resin.

U.S. Pat. No. 4,101,338 (Rapaport et al.) discloses a method of separating salts and sucrose present in blackstrap molasses obtained from sugar cane by ion exclusion chromatography. Prior to ion exclusion chromatography, the molasses are treated by removing organic non-sugar impurities and colour. Various methods are suggested for removing these impurities, including a preferred method utilizing precipitation with iron salts, such as ferric chloride or ferric sulfate, to form flocs. The insoluble flocs are then removed from the molasses stream and the soluble iron salts are removed by the addition of lime and phosphoric acid or inorganic phosphate salts, which raises the pH to above 7.0. The molasses stream is then applied to the ion exchange column to produce fractions containing sucrose and separated salts. A disadvantage of this process is that, upon addition, of ferric ions, the molasses has a pH that is in the range of 2.0 to 3.0. At such a low pH, degradation of xylose could occur. Furthermore, Rapaport et al. do not address the separation of acetic acid from sugars.

Organic non-carbohydrate impurities within a lignocellulosic system cannot be removed by the methods of Rapaport et al. According to the method of Rapaport, the amount of solids precipitated by iron salts or ethanol is modest and no solids are removed by centrifugation. By contrast, the sugar streams produced during; the processing of lignocellulosic feedstock have a much higher level of organic non-carbohydrate impurities and inorganic salts. Rapaport, et al. do not address the processing of such concentrated streams.

U.S. Pat. No. 6,709,527 (Fechter et al.) discloses a process of treating an impure cane-derived sugar juice to produce white sugar and white strap molasses. The process involves subjecting the sugar juice to microfiltration/ultrafiltration to decrease the levels of impurities. The sugar juice is next subjected to ion exchange with a strong acid cation exchange resin in the hydrogen form and then to ion exchange with an anion exchange resin in the hydroxide form. After ion exchange, the resulting sugar solution is concentrated to produce syrup which is men crystallized to produce impure crystallized sugar and white strap molasses. Although the process results in the removal of impurities from the sucrose solution, it would be subject to the limitations associated with ion exchange chromatography described above.

U.S. Pat. No. 4,631,129 (Heikkilä et al.) teaches a method of purifying sugar from a sulfite pulping spent liquor stream. The process involves two steps, in which, during the first step, the pH of the spent sulfite liquor is adjusted to below 3.5 and the stream is passed through a strongly acidic ion exclusion resin to recover two lignosulfonate-rich raffinate fractions and a product stream containing the sugar and consisting of 7.8%-55% lignosulfonate. In the second step, the product stream is adjusted to pH 5.5-6.5. The product stream is then filtered, and applied to a second ion exclusion column to further purify the sugar by separating it from the large amount of lignosulfonates in this stream. A problem with this process is that the use of two ion exclusion systems is costly and adds to the complexity of the process. Moreover, Heikkilä et al. do not quantify or address the separation of compounds present during the processing of biomass such as inorganic salts, including sulfate salts, and acetic acid and other organic acids.

Bipp et al. (*Fresenius J. Anal. Chem.*, 1997, 357:321-325) describes the analytical determination and quantification of sugar acids and organic acids from whey powder hydrolyzates by ion exclusion chromatography. The elution was carried out with 0.005 M sulfuric acid (pH of 2.3) at a temperature of 45° C. and 0.05 M (pH of 1.30) and a temperature of 10° C. Although the analysis demonstrated that the method was suitable for the determination and quantification of organic acids, including sugar acids and acetic acid, the temperatures required for the separation would hot be practical in an industrial application. Furthermore, such low pH values would likely result in the production of degradation products.

There is a need for an economical system for detoxifying sugar streams prior to microbial fermentation of the sugar. The development of such a system remains a critical requirement for the overall process to convert lignocellulosic feedstocks to glucose and subsequently to ethanol or other products.

SUMMARY OF THE INVENTION

The present invention relates to a method of obtaining a product sugar stream from cellulosic biomass, more particularly to a method of obtaining a product sugar stream produced from the enzymatic conversion of cellulosic biomass to sugar.

It is an object of the present invention to provide a method of biomass conversion having improved performance.

The present invention provides a process (A) for obtaining a product sugar stream from cellulosic biomass, the process comprising:

a) pretreating the cellulosic biomass at a pH of about 0.4 to about 2.0 by adding one or more than one acid to the cellulosic biomass to hydrolyze a portion of the cellulose and at least a portion of the hemicellulose in the cellulosic biomass to produce a pretreated cellulosic biomass comprising glucose, acetic acid and a sugar monomer selected from the group consisting of xylose, arabinose, mannose, galactose and a combination thereof;

b) adding one or more than one base to the pretreated cellulosic biomass to adjust the pretreated cellulosic biomass to a pH of about 4.0 to about 6.0, thereby producing a neutralized cellulosic biomass comprising inorganic salt and acetate salt;

c) hydrolyzing the neutralized cellulosic biomass with cellulase enzymes to produce a crude sugar stream;

d) separating insoluble residue from the crude sugar stream to produce a clarified sugar stream;

e) treating the clarified sugar stream using ion exclusion chromatography with a cation exchange resin at about pH 5.0 to about 10.0 to produce one or more than one raffinate stream comprising the inorganic salt and acetate salt and a product sugar stream comprising sugar; and f) recovering the product sugar stream.

The present invention also pertains to the process (A) defined above wherein, in the step of treating (step e)), the ion exclusion chromatography is performed at a pH of between about 6 and about 1.0. The ion exclusion chromatography may also be performed at a pH of between about 6.5 and about 10, or between about 6 and about 8.

The present invention also pertains to the process (A) defined above wherein the clarified sugar stream produced in step d) is concentrated prior to or during the step of treating (step e)). The product sugar stream produced in step e) may also be concentrated.

After the step of recovering (step f)), sugar in the product sugar stream may be fermented. Furthermore, sugar in the product sugar stream may be fermented to produce ethanol or lactic acid. The present invention is also directed to the method as just described further comprising a step of recovering the one or more than one raffinate stream.

The present invention also pertains to the process (A) defined above wherein, during the step of treating (step e)), the ion exclusion chromatography is carried out using a Simulated Moving Bed (SMB) system or an Improved Simulated Moving Bed (ISMB) system. The SMB or ISMB system may be operated with 4 to 16, 8 to 12, or, more preferably, 4 to 12 shifts of feed and collection positions per cycle.

The present invention also provides the process (A) defined above wherein the cellulosic biomass is obtained from a feedstock selected from the group consisting of an agricultural waste, corn stover, wheat straw, barley straw, canola straw, oat straw, rice straw, soybean stover, a grass, switch grass, miscanthus, cord grass, reed canary grass, a forestry residue, aspen wood or sawdust, a sugar residue, bagasse and beet pulp. Preferably, the acid is sulfuric acid and the inorganic salt comprises a sulfate salt (which includes a bisulfate salt). The clarified sugar stream may be characterized by having a lignosulfonate content of from about 0 to about 4% of the total dry solids of the clarified sugar stream. The pretreatment may be selected from the group consisting of steam explosion and dilute acid prehydrolysis. The cellulosic biomass feedstock may also be pressed or leached prior to the step of pretreating (step a)).

The unconverted cellulose is enzymatically hydrolyzed using cellulase enzymes. The dosage of the cellulase enzymes may be about 5 to about 50 IU per gram of cellulose.

The present invention also pertains to the process (A) as defined above wherein, in the step of adding (step b)), the one or more than one base is a soluble base. The soluble base may be selected from the group consisting of sodium hydroxide, potassium hydroxide, ammonia and ammonium hydroxide.

The present invention also pertains to the process (A) as defined above wherein the insoluble residue is separated from the crude sugar stream by microfiltration, plate and frame filtration, crossflow filtration, pressure filtration, vacuum filtration or centrifugation.

The present invention also provides a process (B) for producing ethanol comprising:

a) obtaining cellulosic biomass from a feedstock selected from the group consisting of an agricultural waste, corn stover, wheat straw, barley straw, canola straw, oat straw, rice straw, soybean stover, a grass, switch grass, miscanthus, cord grass, reed canary grass, a forestry residue, aspen wood or sawdust, a sugar residue, bagasse and beet pulp;

b) pretreating the cellulosic biomass at a pH of about 0.4 to about 2.0 by adding one or more than one acid to the cellulosic biomass to hydrolyze a portion of the cellulose and at least a portion of the hemicellulose in the cellulosic biomass to produce a pretreated cellulosic biomass comprising glucose, acetic acid and a sugar monomer selected from the group consisting of xylose, arabinose, mannose, galactose and a combination thereof;

c) adding one or more than one base to the pretreated cellulosic biomass to adjust the pretreated cellulosic biomass to a pH of about 4.0 to about 6.0, thereby producing a neutralized cellulosic biomass comprising inorganic salt and acetate salt;

d) hydrolyzing the neutralized cellulosic biomass with cellulase enzymes to produce a crude sugar stream;

e) separating insoluble residue from the crude sugar stream to produce a clarified sugar stream;

f) treating the clarified sugar stream using ion exclusion chromatography with a cation exchange resin at a pH from about 5.0 to about 10.0 to produce one or more than one raffinate stream comprising the inorganic salt and acetate salt and a product sugar stream comprising sugar;

g) recovering the product sugar stream, and the one or more than one raffinate stream; and h) fermenting the sugar in the product sugar stream to ethanol or lactic acid.

The present invention also pertains to the process defined (B) above wherein, in the step of treating (step f)), the ion exclusion chromatography is performed at a pH of between about 6 and about 11. Preferably, the ion exclusion chromatography is performed at a pH of between about 6.5 and about 10, or between about 6 and about 8.

The present invention also pertains to the process defined (B) above wherein the clarified sugar stream produced in step e) is concentrated prior to or during die step of treating (step f)). The product sugar stream produced in step f) may also be concentrated.

In the step of pretreating (step b)), pretreatment is selected, from the group consisting of steam explosion and dilute acid prehydrolysis. Preferably, the acid is sulfuric acid and the inorganic salt comprises a sulfate salt (which includes a bisulfate salt). The dosage of cellulase enzymes may be about 5 to about 50 IU per gram of cellulose.

In the step of separating (step e)), the insoluble residue may be separated from the crude sugar stream by microfiltration, plate and frame filtration, crossflow filtration, pressure filtration, vacuum filtration or centrifugation. The clarified sugar stream may be characterized by having a lignosulfonate content of from about 0 to about 4% of the total dry solids of the clarified sugar stream. Additionally, prior to the step of pretreating (step b)), the cellulosic biomass feedstock may be pressed or leached.

The present invention pertains to the process (B) defined above wherein, in the step of treating (step f)), the ion exclusion chromatography is carried out using a Simulated Moving Bed (SMB) system or an Improved Simulated Moving Bed (ISMB) system. The ion exclusion chromatography may be performed at a pH of between about 6 and about 8. Furthermore, the SMB or ISMB system may be operated with 4 to 16, 8 to 12, or 4 to 12 shifts of feed and collection positions per cycle.

The present invention also pertains to the process (B) defined above wherein, in the step of recovering (step g)), the raffinate stream is recovered as a fertilizer.

The present invention also provides a process (C) for obtaining a product sugar stream from a crude sugar stream, the crude sugar stream produced from conversion of cellulosic biomass to sugar, the process comprising:
a) treating the crude sugar stream using ion exclusion chromatography at about pH 5.0 to about 10.0 to produce one or more than one raffinate stream comprising sulfate and acetate salts, and a product stream comprising sugar; and
b) obtaining the product sugar stream.

The present invention includes the process as defined above (C) wherein, after the step of obtaining (step b)), sugar in the product sugar stream is fermented. For example, the sugar in the product sugar stream is fermented to produce ethanol or lactic acid.

The present invention also pertains to the process (C) as defined above wherein, during the step of obtaining (step b)), the one or more man one raffinate stream is recovered.

The present invention includes the process (C) defined above wherein, during the step of treating (step a)), the ion exclusion chromatography is carried out using a Simulated Moving Bed (SMB) system or an Improved Simulated Moving Bed (ISMB) system.

The present invention further includes the process (C) as defined above wherein the crude sugar stream is characterized as having a lignosulfonate content of from about 0 to about 10% of the total dry solids present in the crude sugar stream.

Furthermore, the cellulosic biomass used within the process (C) as defined above may be obtained from a feedstock selected from the group consisting of an agricultural waste, corn stover, wheat straw, barley straw, canola straw, rice straw oat straw, soybean stover, a grass, switch grass, miscanthus, cord grass, reed canary grass, a forestry residue, aspen wood or sawdust, a sugar residue, bagasse and beet pulp. The feedstock is preferably pretreated with acid to convert cellulose, a portion of the cellulose, hemicellulose, a portion of the hemicellulose, or a combination thereof, to sugar and produce the crude stream. The pretreatment of the cellulosic biomass may be selected from the group consisting of steam explosion, dilute acid prehydrolysis, and pressurized liquid water. The cellulosic biomass feedstock may also be pressed or leached prior to the pretreatment.

The removal of the impurities allows the sugar streams to be fermented more easily. This allows a higher yield of ethanol or other products to be achieved. Alternatively, a similar yield can be achieved in a shorter time, or using a smaller fermentation vessel, than otherwise would be required. The inorganic salts, acetate salts and other impurities can be recovered and available for sale as by-products, which potentially increase the revenues from the process.

This process overcomes the disadvantages of the prior art by operating the ion exclusion at a much higher pH range than that previously reported for biomass sugar systems. At this high pH range, the acetic acid produced during the pretreatment exists as its acetate salt and the acids introduced during the step of pretreatment are present in their salt form. Consider, for example, when sulfuric acid is employed during pretreatment. Increasing the pH of the resulting sugar stream increases the concentration of the inorganic sulfate salts. Analogous inorganic salts are formed with the use of other acids. At pH values of about 5-10, the inorganic salts and acetate salts are excluded by the cation exclusion resin. This results in a similar elution of the inorganic and acetate salts at pH 5 to 10, thereby eliminating the need for using three streams to recover inorganic acid, acetic acid and sugar that is required at more acidic conditions. This, in turn, increases the sugar recovery and decreases the complexity of the system. The process of the invention is capable of 98.5% or higher sugar recovery, a significant improvement over the 92% recovery reported in the prior art at acidic pH.

Therefore, the invention offers significant advances in the purification of sugar and recovery of inorganic and acetate salts and acids during the conversion of lignocellulosic feedstocks.

This summary of the invention does not necessarily describe all necessary features of the invention.

BRIEF DESCRIPTION OF THE DRAWINGS

These and other features of the invention will become more apparent from the following description in which reference is made to the appended drawings wherein:

FIG. 2 shows separation of glucose, and sodium sulphate and sodium acetate using ion exclusion chromatography at different pH values.

FIG. 5 shows the separation of xylose from salts in a biomass conversion process using ion exclusion chromatography performed at pH 5.

DESCRIPTION OF PREFERRED EMBODIMENTS

Figure 1:
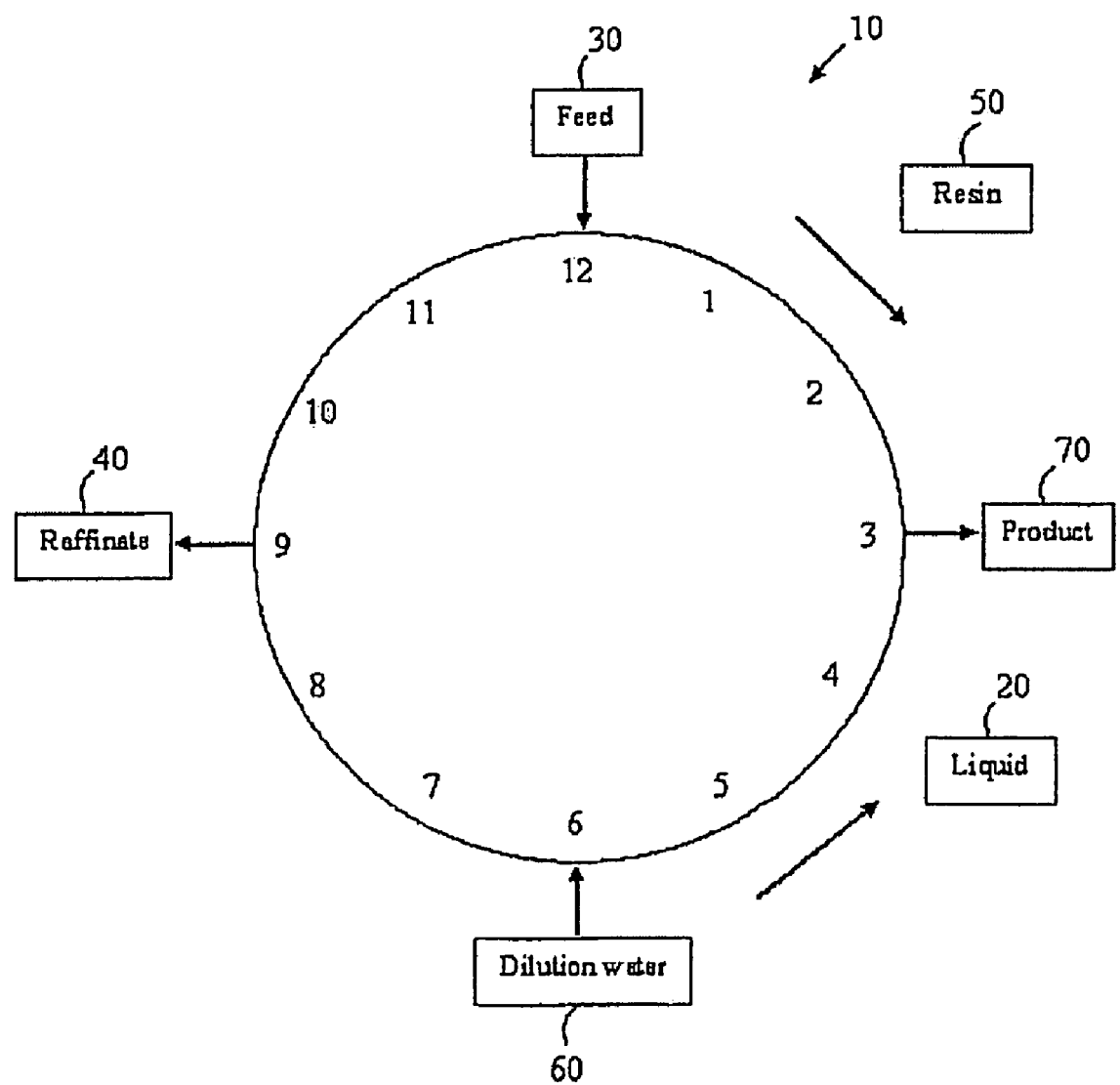
FIG. 1 shows a representation, of the zones and liquid flows in, a Simulated Moving Bed (SMB) system.

The present invention relates to a method of obtaining a product sugar stream from cellulosic biomass, more, particularly to a method of obtaining a product sugar stream produced from the enzymatic conversion of cellulosic biomass to sugar.

The following description is of a preferred embodiment.

The process of the present invention allows for the removal of sulfuric acid, acetic acid, salts, and other impurities from crude sugar streams that originate during the conversion of a lignocellulosic feedstock to sugar. The insoluble residue in the crude sugar stream is removed to produce a clarified sugar stream that undergoes ion exclusion chromatography at about pH 5.0 to alkaline pH, for example from a pH of about 5 to about 10, or any amount therebetween. By operating at this pH range, sugars are collected in a high-binding product sugar stream, and other impurities are collected in one or more than one low-binding raffinate stream. The product sugar stream can then be fermented by microbes to produce ethanol, lactic acid, or other fermentation products.

The present invention provides for a process for purifying a crude sugar stream that may be suitable for further processing, for example but not limited to, a fermentation feedstock, a growth media, or other uses. The process comprises:

a) pretreating the cellulosic biomass at a pH of about 0.4 to about 2.0 by adding one or more than one acid to the cellulosic biomass to hydrolyze a portion of the cellulose and at least a portion of the hemicellulose in the cellulosic biomass to produce a pretreated cellulosic biomass comprising glucose, acetic acid and a sugar monomer selected from the group consisting of xylose, arabinose, mannose, galactose and a combination thereof;

b) adding one or more than one base to the pretreated cellulosic biomass to adjust the pretreated cellulosic biomass to a pH of about 4.0 to about 6.0, thereby producing a neutralized cellulosic biomass comprising inorganic salt and acetate salt;

c) hydrolyzing the neutralized cellulosic biomass with cellulase enzymes to produce a crude sugar stream;

d) separating insoluble residue from the crude sugar stream to produce a clarified sugar stream;

e) treating the clarified sugar stream, using ion exclusion chromatography with a cation exchange resin at about pH 5.0 to about 10.0 to produce one or more than one raffinate stream comprising the inorganic salt and acetate salt and a product sugar stream comprising sugar; and f) recovering the product sugar stream.

The present invention also provides for a process for producing ethanol comprising:

a) obtaining cellulosic biomass from a feedstock selected from the group consisting of an agricultural waste, corn stover, wheat straw, barley straw, canola straw, oat straw, rice straw, soybean stover, a grass, switch grass, miscanthus, cord grass, reed canary grass, a forestry residue, aspen wood or sawdust, a sugar residue, bagasse and beet pulp;

b) pretreating the cellulosic biomass at a pH of about 0.4 to about 2.0 by adding one or more than one acid to the cellulosic biomass to hydrolyze a portion of the cellulose and at least a portion of the hemicellulose in the cellulosic biomass to produce a pretreated cellulosic biomass comprising glucose, acetic acid and a sugar monomer selected from the group consisting, of xylose, arabinose, mannose, galactose and a combination thereof;

c) adding one or more than one base to the pretreated cellulosic biomass to adjust the pretreated cellulosic biomass to a pH of about 4.0 to about 6.0, thereby producing a neutralized cellulosic biomass comprising inorganic salt and acetate salt;

d) hydrolyzing the neutralized cellulosic biomass with cellulase enzymes to produce a crude sugar stream;

e) separating insoluble residue from the crude sugar stream to produce a clarified sugar stream;

f) treating the clarified sugar stream using ion exclusion chromatography with, a cation exchange resin at a pH from about 5.0 to about 10.0 to produce one or more than one raffinate stream comprising the inorganic salt and acetate salt and a product sugar stream comprising sugar;

g) recovering the product sugar stream, and the one or more than one raffinate stream; and h) fermenting the sugar in the product sugar stream to ethanol or lactic acid.

The present invention also provides a process for obtaining a product sugar stream from a crude sugar stream, the crude sugar stream produced from conversion of cellulosic biomass to sugar, the process comprising:

a) treating the crude sugar stream using ion exclusion chromatography at about pH 6.0 to about 10.0 to produce one or more than one raffinate stream comprising sulfate; and acetate, salts, and a product stream comprising sugar; and b) obtaining the product sugar stream.

The sugar in the product sugar stream may fermented, for example to produce ethanol or lactic acid.

The crude sugar stream is the product of the conversion of a lignocellulosic feedstock to sugar by hydrolysis. By the term "lignocellulosic feedstock", "lignocellulosic biomass", "cellulosic biomass", or "biomass feedstock", it is meant any type of biomass comprising cellulose. Cellulosic biomass can consist of an entire plant or a portion thereof, or a mixture of plants or portions thereof, whichever may be the source of crude sugar for the process. The process of the invention is effective on a wide variety of biomass feedstocks, including: (1) agricultural wastes such as corn stover, corn fiber, wheat straw, barley straw, canola straw, oat straw, rice straw, and soybean stover; (2) grasses such as switch grass, miscanthus, cord grass, and reed canary grass; (3) forestry residues such as aspen wood and sawdust; (4) sugar residues, such as bagasse or beet pulp; and any combination thereof.

Cellulosic biomass comprises cellulose in an amount greater than about 20%, more preferably greater than about 30%, more preferably greater than about 40% (w/w), still more preferably greater than 50% (w/w). For example, the lignocellulosic material may comprise from about 20% to about 50% (w/w) cellulose, or more, or any amount therebetween.

The preferred sugar streams used with the method of the present invention result from the conversion of the cellulosic feedstocks. It is also preferred that these feedstocks do not comprise molasses or spent sulfite liquor. Greater than about 80%, preferably greater than about 85% or 90% of the sugar in the sugar stream is the result of hydrolysis of cellulose and hemicellulose in the cellulosic feedstock. For example, 80, 82, 85, 87, 90, 92, 95, 97, or 100% of the sugar in the sugar stream may be derived from cellulose and hemicellulose. Furthermore, it is preferred that at least 50, 55, 60, 65, 70, 75, 80, 85 or 90 wt % of the cellulose in the biomass is converted to glucose.

The sugars may be produced by any method known in the art, for example, but not limited to, subjecting the feedstock to acid hydrolysis (e.g. as disclosed in Brennan et al, Biotech. Bioeng. Symp. No. 17, 1986, which is incorporated herein by reference). The acid hydrolysis may be carried out to convert the cellulose to glucose, convert a portion of the cellulose to glucose, convert the hemicellulose to its monomeric sugars of xylose, arabinose, galactose, mannose, convert a portion of the hemicellulose to its monomeric sugars, or a combination thereof. The acid used for hydrolysis may be any type of suitable acid known in the art, including, but not limited to, sulfuric acid. Sulfuric acid may be used in a dilute form from about 0.1% to about 5% on weight of feedstock or any amount therebetween, or the sulfuric acid may be used in a concentrated form, for example, submersing the feedstock in from about 30% to about 80%, or any amount therebetween, solution of acid, by weight. It is preferred that the crude sugar stream is characterized as having a lignosulfonate content of less than 10% of the total dry solids of the crude sugar stream. For example, crude sugar streams characterized as having an amount of lignosulfonate from about 0 to about 10% of the total dry solids of the crude sugar stream, or about 10, 8, 6, 4, 2, 1 or 0% of the total dry solids of the crude, sugar stream, may be used in the process described herein.

Alternatively, the biomass feedstock may be subjected to a pretreatment process to convert hemicellulose, a portion of the cellulose, a portion of the hemicellulose, or any combination thereof, to sugar, and the remaining cellulose may then be converted to glucose by enzymatic hydrolysis with cellulase enzymes. The step of pretreatment increases the susceptibility of the cellulosic biomass to hydrolysis by cellulase enzymes. The pretreatment is carried out to convert at least a portion of hemicellulose to xylose, arabinose, galactose, mannose and a small portion of the cellulose to glucose, and the remaining cellulose is then converted to glucose by enzymatic hydrolysis with cellulase enzymes. A non-limiting example of such a treatment includes steam explosion, as described in U.S. Pat. No. 4,461,648 (Foody; which is incorporated herein by reference). Generally, pretreatment conditions for lignocellulosic feedstocks comprise a temperature in the range of about 170° C. to about 260° C., or, any amount therebetween, for a period of about 0.1 to about 30 minutes or any amount therebetween, and at a pH of about 0.4 to about 2.0 or any amount therebetween.

Examples of other pretreatment processes that are suitable for the practice of this invention, which are not to be considered limiting, include those described in U.S. Pat. No. 5,535,325; U.S. Pat. No. 4,237,226; and Grethlein, *J. Appl. Chem. Biotechnol*, 1978, 28:296-308; which are incorporated herein by reference. After pretreatment, the pH of the material is adjusted to the appropriate range prior to enzymatic hydrolysis.

The low pH for pretreatment requires the addition of acid to the feedstock. Typically a dilute acid, added to achieve a final concentration in the feedstock from about 0.02% (w/v) to about 3% (w/v), or any amount therebetween, is used for the pretreatment. The acid used for pretreatment may be any type of suitable acid known in the art, including, but not limited to, sulfuric acid, or phosphoric acid. Sulfuric acid is preferred due to its low cost and, following recovery, its use in fertilizer in the form of sulfate salts. The term "sulfate salts" includes bisulfate salts that are also presents at a concentration that depends on the pH.

Cellulase enzymes can typically tolerate a range of pH of about 4 to 6; therefore, the pretreated feedstock is generally neutralized prior to enzymatic hydrolysis. A pH more favorable to the cellulase enzymes is, for example, within the range of about 4.5 to about 5.0, or any value therebetween. The pH-adjusted, pretreated feedstock can then be subjected to enzymatic hydrolysis using cellulase enzymes.

The term "base" is meant to encompass any soluble species that, when added to water, gives a solution with a pH that is more than 7, and which is suitable for neutralizing the pretreated feedstock to a pH value that is compatible with enzymes used during enzymatic hydrolysis.

Preferably, the pH adjustment is carried out using a soluble base. By the terra "soluble base", it is meant a base that has a solubility in water that is at least 0.1 M at 20° C. This term is meant to exclude salts that are slightly soluble or insoluble. Examples of insoluble bases that are excluded from the definition of soluble base are $CaCO_3$ and $Ca(OH)_2$. Non-limiting examples of soluble bases include sodium hydroxide, potassium hydroxide, ammonia, and ammonium hydroxide.

By the term "cellulase enzymes", "cellulase", or "enzymes", if is meant enzymes that catalyse the hydrolysis of cellulose to products such as glucose, cellobiose, and other cellooligosaccharides. Cellulase is a generic term denoting a multienzyme mixture, produced by a number of microorganisms, comprising exo-cellobiohydrolases (CBH), endoglucanases (EG) and β-glucosidases (βG). Among, the most widely studied, characterized, and commercially produced cellulases are those obtained from fungi of the genera *Aspergillus*, *Humicola*, and *Trichoderma*, and from the bacteria of the genera *Bacillus* and *Thermobifida*. In a non-limiting example, the pretreated feedstock described above may be submitted to hydrolysis by cellulase enzymes produced by *Trichoderma*.

The cellulase enzyme dosage is chosen to convert the cellulose of the feedstock to glucose. For example, an appropriate cellulase dosage can be about 5.0 to about 50.0 Filter Paper Units (FPU or IU) per gram of cellulose, or any amount therebetween. For example, the cellulase dosage may be about 5, 8, 10, 12, 15, 18, 20, 22, 25, 28, 30, 32, 35, 38, 40, 42, 45, 48, or 50 FPU, or any amount therebetween. The FPU is a standard measurement which is familiar to those skilled in the art and is defined and measured according to Ghose (*Pure and Appl. Chem.*, 1987, 59:257-268).

The acid requirement for pretreatment may be decreased by removing salts from the feedstock prior to pretreatment. Salts may be removed by washing, leaching, or a combination of these processes. One form of the leaching process is taught in WO 02/070753 (Griffin et al., which is incorporated herein by reference). This process involves contacting the feedstock with water for two minutes or longer, then separating the solids from the aqueous phase ("leachate") by pressing or filtration. After leaching, the aqueous phase contains, potassium and other salts and trace elements. This process may not only decrease costs, but may also decrease the degradation of xylose in the pretreatment process.

The crude sugar streams of the present invention resulting from the breakdown of the biomass feedstocks, as described above may contain water as a primary component. The amount of water present in the crude sugar streams may be an amount in the range of about 40% to about 95% (w/w), or any amount therebetween. Preferably, the crude sugar stream may comprise from about 50% to about 85% (w/w) water, or any amount therebetween, arising from a step of concentration.

Concentration of the crude sugar stream may be carried out using any technique known to those of skill in the art. For example, concentration may be carried out by subjecting the crude sugar stream to membrane filtration, evaporation, or a combination thereof. Without being limiting, microfiltration (with a pore size of 0.05 to 5 microns) may be carried out to remove particles, followed by ultrafiltration (500-2000 raw cut off) to remove soluble lignin and other large molecules and reverse osmosis to increase the solids to a concentration of about 12 to about 20%, or any amount therebetween, followed by evaporation.

The sugar stream should not contain any significant amount of insoluble compounds, as the insoluble compounds foul the ion exclusion chromatography system. Any suitable method for removing insoluble residue from the crude sugar streams to produce a clarified sugar stream can be employed as would be known by one of skill in the art. This includes, but is not limited to, microfiltration, plate and frame filtration, crossflow filtration, pressure filtration, vacuum filtration, centrifugation, and the like.

It is preferred that the clarified sugar stream is characterized as having a lignosulfonate content of less than 4% of the total dry solids of the clarified sugar stream. For example, the clarified sugar streams may be characterized as haying an amount of lignosulfonate from about 0 to about 4% of the total dry solids of the clarified sugar stream.

The soluble compounds in the clarified sugar stream may include monomeric sugars such as glucose, xylose, arabinose, galactose, mannose, and oligomers of these sugars; acetic acid, sulfuric acid, lactic acid, oxalic acid, among other organic acids, and the salts of these acids; cations including sodium, calcium, potassium, ammonium, magnesium, and others; anions, in addition to the organic acids named above, including silicate, phosphate, and carbonate. Preferably, the solids in the clarified sugar stream are comprised of at least 30 wt % sugar; for example, the solids in the clarified sugar stream may comprise more than 30, 35, 40, 45, 50, 55, 60, 65, 70, 75, 80, 85, 90, or 95 wt % sugar. It is also preferred that the minimum concentration of acetic acid and acetate salts in the clarified sugar stream is about 5 g/L. A variety of other, compounds are present in the clarified sugar stream, including sugar degradation products such as furfural and hydroxymethyl furfural, and soluble phenolic compounds derived from lignin. Organic extractive compounds, such as soaps and fatty acids, are also present.

As described in more detail below, clarified sugar streams are treated by ion exclusion chromatography to separate sugars and other nonionic compounds from the salts and other ionic compounds. Ion exclusion chromatography is preferably carried out at about neutral to alkaline pH. For example, the pH may be in the range of about 5.0 to about 10.0, or any pH value therebetween, for example at a pH from about 6.0 to about 10.0, a pH from about 6.5 to about 10, a pH from about 6 to about 8, or at a pH of about 5.0, 5.2, 5.5, 5.7, 6.0, 6.2, 6.5, 6.7, 7.0, 7.2, 7.5, 7.7, 8.0, 8.2, 8.5, 8.7, 9.0, 9.2, 9.5, 9.7, 10.0. To maintain the desired pH range of 5 to 10, the clarified feed stream may be adjusted to this pH range. Those of skill in the art will be aware of chemicals suitable for adjusting the pH of the clarified sugar stream, for example but not; limited to, ammonium hydroxide, sodium hydroxide, potassium hydroxide, ammonia or sulfuric acid.

Figure 2A:
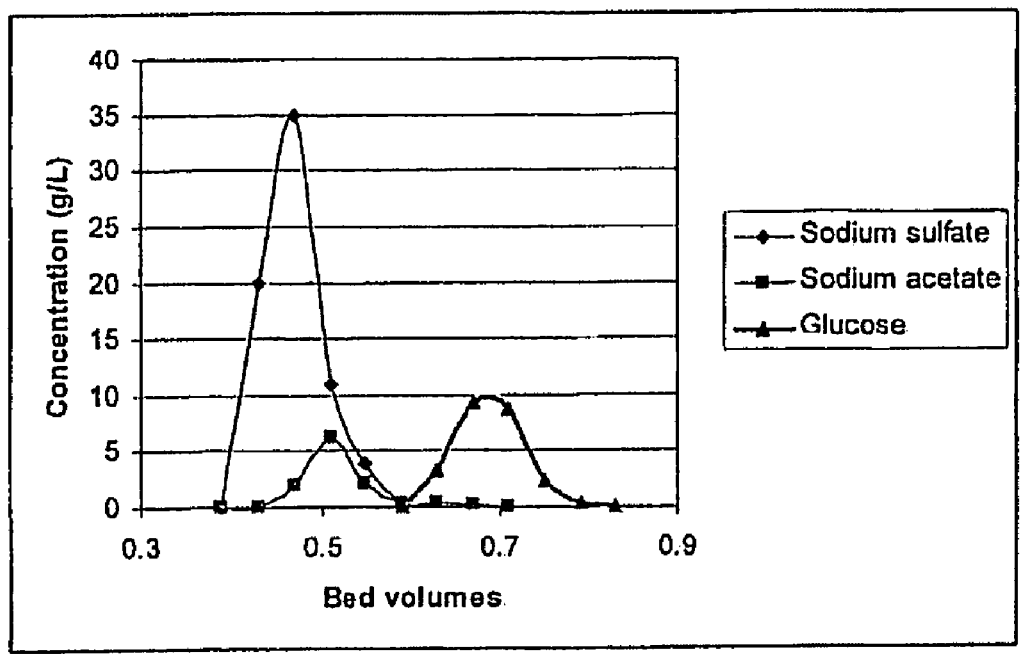
FIG. 2A shows the elution of sodium sulfate, sodium acetate, and glucose at pH 8.
Figure 2B:
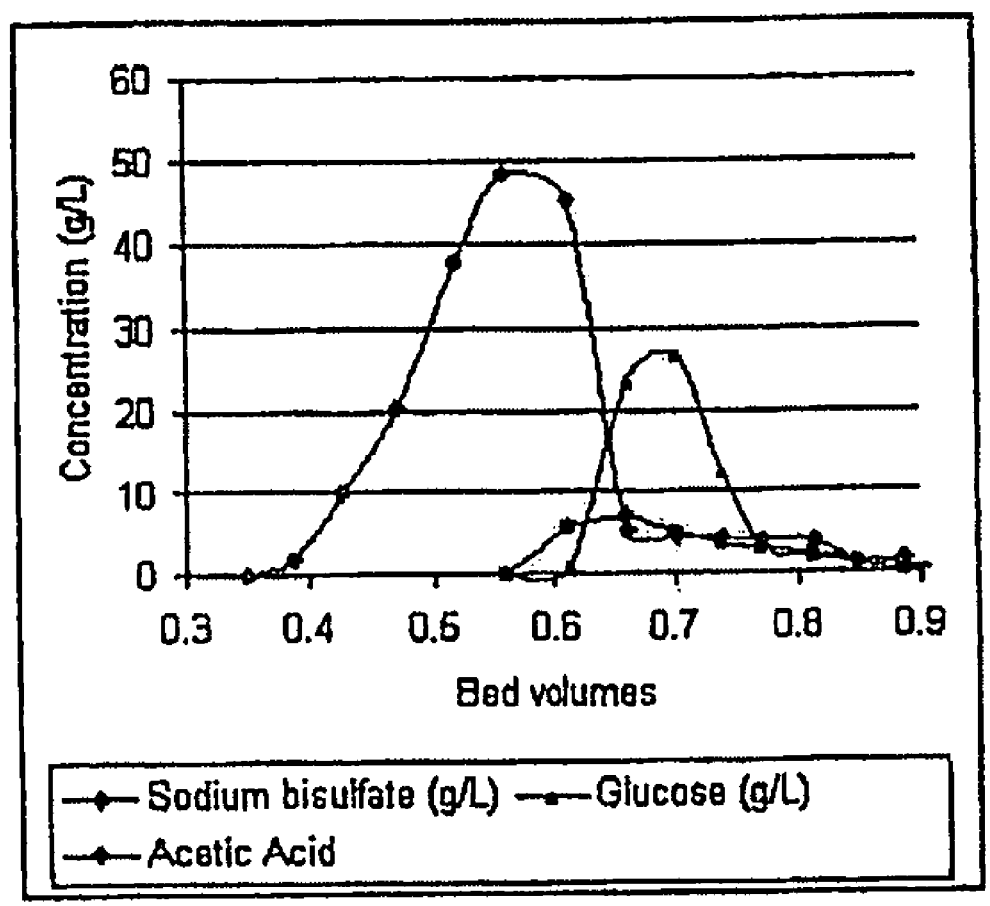
FIG. 2B shows the elution of sodium bisulfate, acetic acid, and glucose at pH 3.

The separation of sugar from sodium sulfate and sodium acetate at an alkaline pH following methods of the present invention is shown in FIG. 2A (Example 1). In addition, the separation of sugar from sodium bisulfate and acetic acid that would be present in a sugar stream arising from biomass conversion was carried out at pH 3 following the methods of Example 2. With reference to FIG. 2B, at pH 3, the separation of sugar from sodium bisulfate and acetic acid leads to undesirable separation performance under these conditions as acetic acid co-elutes with the sugar product.

The ion exclusion system of the present invention may be operated in a temperature range of about 20° C. to about 90° C., preferably at a temperature between about 45° C. to about 80° C., or any value therebetween, for example, at a temperature of about 60° C. to about 70° C., or at about 45, 47, 50, 52, 55, 57, 60, 62, 65, 67, 70, 72, 75, 77, 80° C.

The process of ion exclusion chromatography may involve the use of one, or more than one, column filled with ion exchange resin, as is evident to one of skill in the art. For the sake of simplicity, the operation of a single column will be illustrative, but the use of more than one column is also considered to be within the scope of the present invention. The ion exchange resin is a cation exchange resin. Preferably, the resin is a strong cation exchange resin, for example, which is not to be considered limiting, with a polystyrene backbone and 4-8% divinylbenzene crosslinking. These resins have sulfonate functional groups and are available commercially in the sodium form, or, less preferably, in the hydrogen, potassium or ammonium form. The resins are preferably of diameter of from about 0.1 to about 1.0 mm. Cationic exchange resins are available from several vendors, including Dow or Mitsubishi.

The column may be prepared prior to carrying out the separation by converting it into the desired cation-exchange form. This may involve washing a volume of the clarified sugar stream through the column. The volume may be equal to from about 2 to about 5 times the volume of the resin in the column, or the washing may be carried out until the effluent pH matches the pH of the clarified sugar stream. Alternatively, the column may be prepared by washing it with a volume of solution containing cations corresponding to those that would be present in the clarified sugar stream.

Once the column is in the appropriate cation-exchange form, the clarified sugar stream ("feed stream") is applied onto the column. For example, which is not to be considered limiting, a quantity of the clarified sugar stream equal to about 0.05 to about 0.3 times the volume of the column, or any amount therebetween, is applied. However, the amount of the clarified sugar stream to be applied may differ from that just disclosed, and it may be readily determined based on experimentation to determine column capacity and separation. A desired liquid flow rate is also selected as may be readily determined by one of skill in the art, for example, but not limited to, a liquid flow rate corresponding to about 5% to about 70%, or any amount therebetween, of the column volume per hour.

As the clarified sugar stream is applied, the charged ions in the salts and other charged compounds are excluded from the resin and flow through the column. The sugar and other nonionic compounds are not repelled by the charged resin, and penetrate the pores of the resin. The sugar and other nonionic compounds are thereby retained by the resin and elute the column more slowly than the ionic compounds.

After the desired volume of the clarified sugar stream is injected, the feed is switched to water, which may have been previously softened to decrease the concentration of multivalent cations. The ionic compounds contain inorganic salts such as the inorganic salts of the base used for pH adjustment and the inorganic salts of the acid used in pretreatment, as well as acetic acid and other organic acids originating from the cellulosic biomass. The ionic compounds flow through the column and are collected in one or more than one stream. This one or more than one stream is designated as "raffinate" (or one or more than one raffinate) and contains the majority of the inorganic and acetate salts, and trace amounts of sugar. The one or more than one raffinate stream is followed by the elution of sugars arising from the processing of the cellulosic biomass and nonionic compounds, which are collected separately from the one or more than one raffinate. The product sugar stream (product stream) contains most of the sugar and little of the salt and other ionic components.

In a preferred embodiment, the ion exclusion chromatography is carried out by a Simulated Moving Bed (SMB) device. An SMB contains ion exchange resin similar to that in an ion exclusion system described above, and performs the same type of separation of sugars and nonionic compounds in the product stream and salts and other ionic compounds in the raffinate stream. For a given feed stream, an SMB is run at the same pH and temperature as an ion exclusion system.

However, an SMB system has distinct locations for feeding of the clarified sugar stream, feeding of dilution water, and withdrawal of sugar product and of the one or more than one raffinate streams. For example, which is not to be considered limiting, four flow locations equally spaced apart may be used on one or more than one column. The order of the locations, is, arbitrarily starting from the feed inlet, 1) the clarified sugar stream feed, 2) the raffinate withdrawal, 3) the dilution water feed, and 4) the product withdrawal. If a single column is used, the outlet from the top of the column may be used to feed the bottom, thus completing a circle. If more than one column is used, which is typical, the outlet of each column feeds the next column, again producing a circle of flow. The SMB is therefore much more of a fully continuous operation than a single-column ion exclusion system. Additional flow locations may be included if more than one raffinate stream is to be collected.

Another difference between an SMB and a single-column ion exclusion system is that the SMB has a recirculation flow that supplements and is co-current with all of the other flow streams. This recirculation flow is carefully chosen, along with the other flows, to provide the optimum separation between the sugar and salt streams.

Additionally, an SMB system simulates movement of the resin bed in a direction opposite to that of the liquid flow. With reference to FIG. 1, the simulated movement is carried out by periodically shifting the four flow locations by some fraction of the total bed. For example, if an SMB system is visualized as a circular system 10, for example a clock, then liquid 20 flows counterclockwise in this system. The 12 hourly positions on the clock can symbolize an SMB with 12 zones, with the feed 30 set arbitrarily at 12 O'clock. As the liquid flows around, the raffinate 40, which has a low affinity for the resin 50, is withdrawn at 9 O'clock. Dilution water 60 is added at 6 O'clock at a flow rate that is from about 1.0 to about 4.0 fold the feed application rate. In a preferred embodiment, the dilution water flow is added at from about 1.0 to about 1.5 times the feed flow rate. The bound compounds do not have a high enough affinity to remain bound at the high flow rates present after the dilution water 60 is added. These compounds are washed off the resin 50 at the product stream withdrawal 70, positioned at 3 O'clock. After the product withdrawal 70, a relatively clean stream flows back up to 12 O'clock to continue the cycle.

At a chosen interval of perhaps 10 minutes to 4 hours, preferably 15 minutes to 2 hours, die stream positions (flow locations) are shifted clockwise to simulate movement of the bed. If the positions are shifted by 1 hour in location, the feed 30 is then at 1 O'clock, product 70 at 4 O'clock, dilution water at 7 O'clock, and raffinate 40 at 10 O'clock, and this system has shifted 1/12 in position.

The bed positions are shifted at a frequency and to a degree that are chosen to optimize the separation of interest which depends on the affinity that the sugar and salt have for the resin, the liquid flow rates, and the cost of such a switching system. A typical SMB rotates the positions by about 1/16 to about 1/4 of the extent of the cycle, thereby defining from about 16 to about 4 zones, respectively. The 4-to-16 zones can be carried out on a single column. In a preferred embodiment, one column is used. This simplifies the demarcation of zones and allows for a given column to be brought off line, for cleaning or maintenance without overly disturbing the operation. For example, which is not to be considered limiting, from about 4 to about 16 columns may be used. In a more preferred embodiment, about 4 to about 8 columns are used. However, the number of columns may be adjusted as required.

Improved SMB ("ISMB") systems (available for example from Eurodia Industrie S.A., Wissous, France; Applexion S.A., Epone, France; or Amalgamated Research Inc., Twin Falls, Id.) may also be used as described herein. ISMB systems include variable flow rates of feed, dilution water, product, raffinate, or a combination thereof, or sequential periods with one or more streams closed off, with or without recirculation of the liquid in the columns, or a combination of two or more of these features. The present invention can be practiced with ISMB or SMB operations.

The clarified sugar stream, the product sugar stream obtained after ion exclusion chromatography, or both streams, may be concentrated. Any suitable method may be utilized for concentrating the product sugar stream or clarified sugar stream. This includes the methods described above for concentrating the crude sugar stream.

The product sugar stream obtained following ion exclusion chromatography is readily fermented. Prior to fermentation, the product sugar stream may be adjusted to a pH from about 4 to about 6, as desired for the particular fermentation. The product sugar stream may be concentrated by evaporation, filtration, or other methods familiar to those skilled in, the art, prior to fermentation.

In a preferred embodiment, the sugar in the product sugar stream is fermented to ethanol. Fermentation may be carried out by yeast, bacteria or other microbes capable of fermenting the product stream to a desired efficiency and yield. In a preferred embodiment, the fermentation is carried out using a genetically engineered yeast, for example, but not limited to, *Saccharomyces* or *Pichia*, or bacteria, for example, but not limited to, *Zymomonas* or *E. coli* capable of fermenting the pentose sugars xylose, arabinose, or a combination thereof, in addition to the hexose sugars glucose, mannose, galactose, or a combination thereof. Alternatively, the sugar in the product sugar stream is fermented to lactic acid. Those skilled in the art are familiar with the requirements in fermentation of sugar to produce ethanol, lactic acid or other products.

The inorganic salt in the raffinate stream may be crystallized, dried or subjected to electrodialysis or agglomeration and granulation, and used as desired, for example, as a solid fertilizer. Alternatively, the inorganic salt may be concentrated as a wet slurry and used in a liquid form, for example, as a liquid fertilizer. Processing of inorganic salt stream may be carried out as described in co-pending U.S. patent application entitled "Recovery of Inorganic Salt During Processing of Lignocellulosic Feedstock", which is incorporated herein by reference.

Ammonium, potassium, sulfate, and phosphate salts in the raffinate stream are typically of value. Other compounds present, including salts of sodium and sulfite salts, may be of less value in fertilizer. However, these salts can be converted to forms of higher value. For example, which is not to be considered limiting, sodium salts can be converted to ammonium salts or potassium salts by the use of ion exchange, which is familiar to those skilled in the art. In this example, sodium hydroxide may be used for some or all of the neutralization of sulfuric acid during the processing of a lignocellulosic feedstock, and the sodium ion exchanged with ammonium or potassium using a cation exchange resin. The resulting ammonium or potassium salt may then be of more value as a fertilizer. Additionally, sulfite salts can be converted to sulfate salts by oxidation with air or other oxidizing agent, for example, sulfurous acid or sulfur dioxide.

The present invention will be further illustrated in the following examples.

EXAMPLES

Example 1

Ion Exclusion Separation of Sodium Sulfate, Sodium Acetate, and Glucose

The effectiveness of ion exclusion at pH 8 as a process for the removal of sodium acetate and sodium sulfate salts from glucose is illustrated by this example.

A fixed bed ion exclusion column was filled with Mitsubishi Chemical resin #UBK530. Prior to filling the column, 135 ml of the resin was suspended in 1 liter of deionized water and allowed to settle. The supernatant was decanted and the procedure carried out three times, which was sufficient to remove all visible fine particles. After decanting of the third supernatant, two resin volumes of deionized water were added to the resin, and the slurry was poured onto the 127 ml column. The column contains a hot water jacket, but the jacket was not used, during the resin-loading procedure. The top of the column was sealed with a rubber stopper attached to a water pump. Care was taken to ensure that the seal was airtight.

The packed column was washed with 300 ml of degassed, deionized water. This removed dissolved gases and minimized resin channeling. If the column became overloaded with air bubbles, the resin was back-washed and the column repacked.

Once the column was degassed satisfactorily, water at 70° C. was circulated through the water jacket. The column was washed with water until the temperature of the water bath reached 70° C.

At this point, the resin was prepared with the feed solution (clarified sugar stream). For this experiment, the feed solution was a synthetic sugar, stream of 1% acetic acid, 10% sodium sulfate, and 2.5% glucose (w/w) dissolved in deionized water and adjusted to pH 8.0 with 10N sodium hydroxide. The resulting concentration of sodium ions was 32.4 g/L. A volume of 200 ml of feed solution was fed onto the column at a flow rate of 1 ml/min. The effluent from the column was collected and discarded. If suspended solids formed in the feed, the feed was filtered and the flow restarted.

Once the feed volume of 200 ml was achieved, the column was washed with deionized water. The conductivity of the eluent was measured and the water wash deemed complete when the eluent conductivity matched that of the water feed. At this point, any excess water present on top of the column bed was removed by using a pipette. A weight of 6.4 grams of feed was then added to the top of the bed, and the column sealed with a stopper as before. The pump was started to pump water at a rate of 1 ml/minute. The stopcock was opened at the base of the column and 4 ml fractions collected over 4 minutes. The water feed and fraction collection were continued until 30 fractions had been collected. After the collection of the 30$^{th}$ fraction, the column was washed with 300 ml deionized water prior to the next run. Care was taken to avoid drying of the resin during overnight storage.

The product fractions were analyzed for sodium sulfate, sodium acetate and glucose. For the acetate determination, the samples were adjusted to pH 3-3.5 with dilute sulfuric acid prior to injection into a gas chromatograph and detection as acetic acid.

The results of the elution are shown in FIG. 2A. The sodium sulfate and sodium acetate elute with a large degree of overlap, followed by the elution of glucose. The separation was good, in that there was little glucose with the salts and little salt with the glucose.

Example 2

Comparative Example

Separation of Glucose from Acetic Acid at pH 3

This example illustrates the use of ion exclusion for the separation of sugar from acetic acid and sodium bisulfate at pH 3. The separation of acetic acid from glucose at pH 3.0 is poor as these two components co-elute (see FIG. 2B). The use of the methods as described herein, provide superior separation of acetic acid and sugar.

A fixed bed ion exclusion column was filled with Mitsubishi Chemical resin #UBK530. Prior to filling the column, 135 ml of the resin was suspended in 1 liter of deionized water and allowed to settle. The supernatant was decanted and the procedure carried out three times, which was sufficient to remove all visible fine particles. After decanting of the third supernatant, two resin volumes of deionized water were added to the resin, and the slurry was poured onto the 122-ml column. The column contains a hot water jacket, but the jacket was hot used during the resin-loading procedure. The top of the column was sealed with a rubber stopper attached to a water pump. Care was taken to ensure that the seal was airtight.

The packed column was washed with 300 ml of degassed, deionized water. This removed dissolved gases and minimized resin channeling. If the column became overloaded with air bubbles, the resin was back-washed and the column repacked.

Once the column was degassed satisfactorily, water at 70° C. was circulated through the water jacket. The column was washed with water until the temperature of the water bath reached 70° C.

At this point, the resin was equilibrated with the feed solution. For this experiment, the feed solution was a synthetic sugar stream of 25 g/L acetic acid, 150 g/L sulfuric acid, and 75 g/L glucose dissolved in deionized water and adjusted to pH 3.0 with 10N sodium hydroxide. The resulting concentration of sodium bisulfate was about 190 g/L. A volume of 200 ml of feed solution was fed onto the column at a flow rate of 1.6 ml/min. The effluent from the column was collected and discarded. If suspended solids formed in the feed, the feed was filtered and the flow restarted.

Once the feed volume of 200 ml was achieved, the column was washed with deionized water. The conductivity of the eluent was measured and the water wash deemed complete when the eluent conductivity matched that of the water feed. At this point, any excess water present on top of the column bed was removed by using a pipette. A weight of 6.4 grams of feed was then added to the top of the bed, and the column sealed with a stopper as before. The pump was started to pump water at a rate of 1.6 ml/minute. The stopcock was opened at the base of the column and 4.8 ml fractions collected over 3 minutes. The water feed and fraction collection were continued until 3.0 fractions had been collected. After the collection of the 30$^{th}$ fraction, the column was washed with 300 ml deionized water prior to the next run. Care was taken to avoid drying of the resin during overnight storage.

The product fractions were analyzed for sodium bisulfate concentration, acetic acid, glucose, and dry weight. For the acetic acid determination, the samples were adjusted to pH 3-3.5 with dilute sulfuric acid prior to injection into a gas chromatograph.

The results of the elution are shown in the FIG. 2B. Most of the sodium bisulfate elutes before glucose is recovered. However, a portion of the sodium bisulfate co-elutes, and is present in samples comprising glucose. Furthermore, the separation of glucose and acetic acid is poor, and a significant portion of acetic acid co-elutes with glucose. This is attributed to the non-ionic nature of acetic acid at pH 3, which makes it difficult to separate from glucose at this pH. This is in contrast with Examples 1 and 3 that show a significantly improved separation of sodium sulfate and sodium acetate from glucose at an alkaline pH, for example, but not limited to, pH 8.0.

Example 3

Elution of Biomass Sugars

Figure 3:
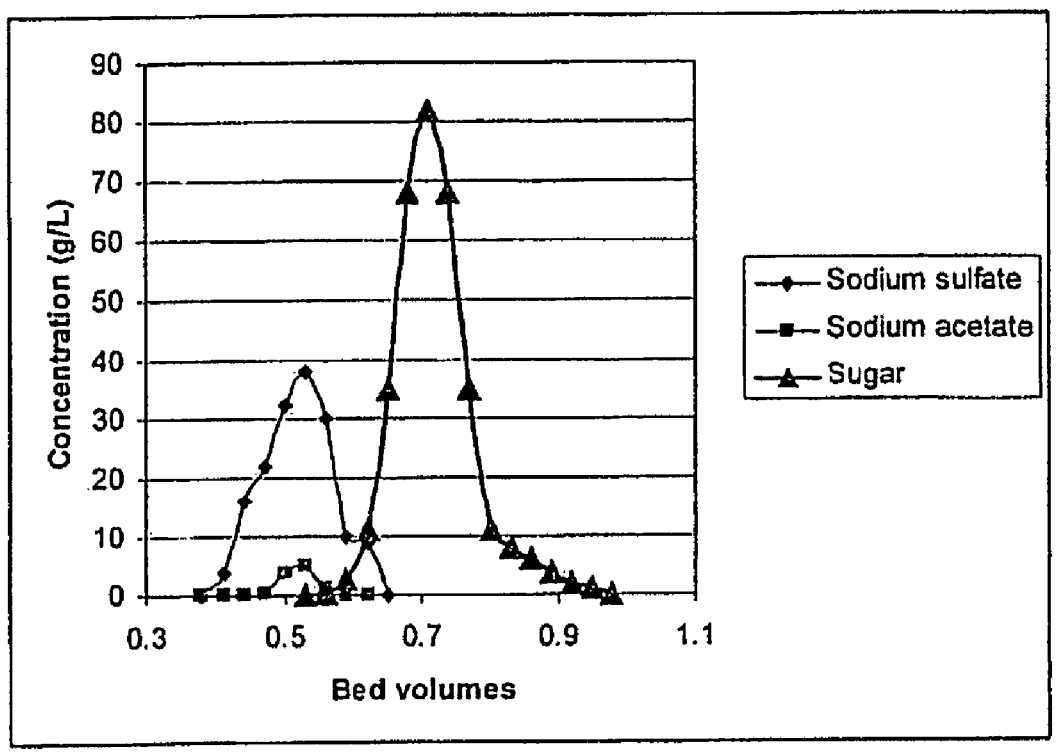
FIG. 3 shows separation of sugar (glucose, xylose and arabinose), sodium sulphate and sodium acetate in a biomass conversion clarified sugar stream using ion exclusion chromatography performed at pH 8.

A feed sample of biomass sugars was made by subjecting wheat straw to pretreatment with sulfuric acid at conditions described in U.S. Pat. No. 4,461,648. The pH of pretreatment was 1.4 and the resulting pretreated feedstock was adjusted to pH 5 with sodium hydroxide. The neutralized cellulosic biomass was subjected to enzymatic hydrolysis by cellulase enzymes made by the fungus *Trichoderma* to produce a crude sugar stream. The crude sugar stream was separated from the insoluble residue, which is primarily lignin, by using plate and frame filtration. The clarified sugar stream was evaporated to 44% total solids, with a concentration of 109 g/L sulfate salts of sodium and potassium, 300 g/L glucose, 44 g/L xylose, 5.3 g/L arabinose, 10.9 g/L sodium acetate (measured as acetic acid), and various trace metals. The clarified sugar stream was evaporated, adjusted to a pH of 8 and then fed to the column and eluted as described in Example 1. The results are shown in FIG. 3.

The ion exclusion system provides a good separation of the sugar from the sodium acetate and sodium sulfate. Almost all of the sugar is in the sugar stream, and almost all of the salt is in the salt stream. This is the case-even when the sugar stream is from a biomass conversion process.

Example 4

Large Scale Purification of Sugars from Cellulose and Fermentation to Produce Ethanol A feed stream of sugars from cellulose; was prepared using the procedures from Example 2 with a concentration of 145 g/L sulfate salts of sodium and potassium, 153 g/L glucose, 49 g/L xylose, 7.3 g/L arabinose, 9.1 g/L sodium acetate (measured as acetic acid), various trace metals, and a significant amount of unidentified impurities. This feed stream was divided into two parts. The first part was diluted 1:3 in water and set aside for fermentation, with a concentration of 48.4 g/L sulfate salts of sodium and potassium, 51 g/L glucose, 16 g/L xylose, 2.6 g/L arabinose, 3.1 g/L sodium acetate. The second part was subjected to large scale ion exclusion chromatography.

The chromatography was carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system consists of 4 columns with 4 bed shifts per cycle and was operated with the feed stream maintained at pH 7.5 to 8.0. The system was maintained at 70° C. as was the sugar feed and the dilution water. The sugar stream was fed at an average rate of 4 liters per minute and dilution water was added at a ratio of 4:1 with the sugar feed. Product and raffinate streams were collected, with the product stream containing 1.6 g/L sulfate salts, 66 g/L glucose, 22 g/L xylose, 3.3 g/L arabinose, and 0.09 g/L acetate (measured as acetic acid).

Both the diluted feed stream and the product stream were pumped into fermentation vessels in liquid volumes of 100 liters and total volume 200 liters. The fermenters were inoculated with 4 g/L yeast strain 1400-LNHST obtained from Purdue University. This strain has been developed to ferment glucose and xylose to ethanol, as described in U.S. Pat. No. 5,789,210. The yield of ethanol for both treated and untreated product streams are provide in Table 1.

TABLE 1

Ethanol yields from treated and untreated sugar streams

| Sugar stream | Ethanol (g/L) after 48 hrs | Ethanol Yield (g/g initial glucose and xylose) |
|---|---|---|
| Diluted, untreated sugars | 12.2 | 0.182 |
| Ion exclusion-treated sugars | 37.9 | 0.431 |

The ion exclusion treated sugar stream was essentially completely fermented by the yeast. Without wishing to be bound by theory, the reduced yield of ethanol produced using the untreated sugar stream may be a result of inhibitors present in this feed stream. The ion exclusion treated stream resulted in a much higher yield of ethanol as shown in Table 1, possibly due to reduced amounts of inhibitors in the ion exclusion-treated stream. This is a demonstration of the detoxification of the sugar stream and the removal of acetate salts, and possibly other inhibitors, by the ion exclusion treatment.

Example 5

Separation of Salts from Xylose at pH 7

Wheat straw was leached according to the methods described in WO 02/070753 (Griffin et al.) to remove inorganic salts. A feedstock sample of biomass sugars was then produced by subjecting, the leached wheat straw to pretreatment with sulfuric acid at conditions described in U.S. Pat. No. 4,461,648 (Foody). The pH of the pretreatment was 1.4 and the pH was adjusted with ammonium hydroxide to a pH value of between 4.5 and 5.0. The pretreated feedstock was subjected to enzymatic hydrolysis by cellulase enzymes made by the fungus *Trichoderma* to produce a crude sugar stream.

The resulting crude sugar stream was separated, from the unhydrolyzed residue, which is primarily lignin, by using plate and frame filtration. After filtering, the clarified sugar stream was evaporated under vacuum at a temperature of between 65 to 75° C. to increase the solids content by 3-4 fold. The concentrated hydrolyzate was then filtered by plate and frame filtration. The glucose in the clarified sugar stream was fermented to ethanol with *Saccharomyces cerevisiae* yeast. While the glucose is easily fermentable, xylose sugars present in the hydrolyzate are more difficult to ferment.

After fermentation, the fermentation broth was filtered and then centrifuged to remove yeast cells. The pH was then adjusted to 7.0 with ammonium hydroxide. The fermentation broth was distilled to produce fuel grade ethanol and still bottoms, which were then evaporated to 13% total solids (w/w). The concentrated still bottoms contained 44 g/L sulfate salts of sodium, potassium and ammonium, 0.4 g/L glucose, 12.1 g/L xylose, 0.3 g/L arabinose, 9.3 g/L acetic acid, and various trace metals. The still bottoms were then adjusted to pH 7 with a small volume of 1 M NaOH and filtered. Ion exclusion chromatography of the concentrated still bottoms was performed as in Example 1, except that ammonium sulfate was passed through the column prior to addition of the sugar stream to convert the resin into the ammonium form.

The total solids content of each fraction were measured by placing 1 nil from each fraction in a pre-weighed aluminum tray and allowing them to evaporate in an oven at 100° C. for at least an hour. The trays were allowed to cool briefly before being re-weighed, and the mass difference was divided by the volume to obtain the concentration of total dissolved solids in g/L.

For xylose analysis, an aliquot of each fraction that contained dissolved solids was assayed for reducing sugars using the DNS (3,5-dinitrosalicylic acid) method described by Miller, G. L. (*Anal. Chem.*, 1959, 31:426).

Figure 4:
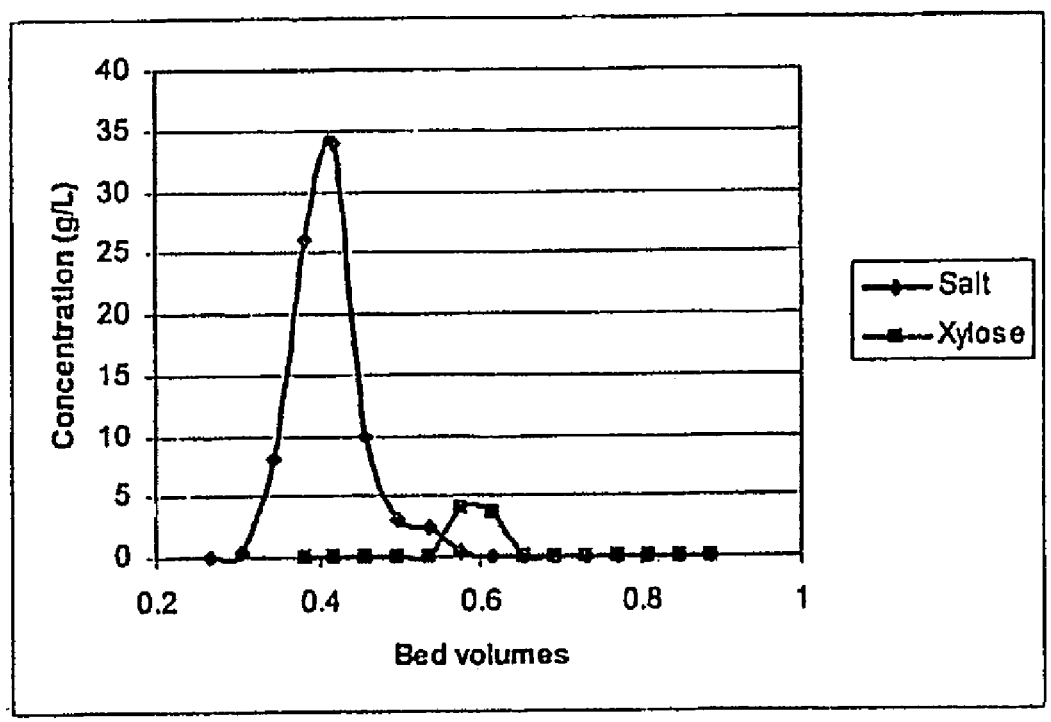
FIG. 4 shows the elution of xylose and salts in a biomass conversion process stream using ion exclusion chromatography performed at pH 7.

The results of the elution are shown in FIG. 4. Salt eluted first, followed by the elution of xylose. The separation was good in that little xylose eluted with the salts and little salt eluted with the xylose.

The purified xylose is then fermented to ethanol by a yeast strain that can convert xylose to ethanol. An example of such a strain is that described in U.S. Pat. No. 5,789,210 (Ho et al.).

Example 6

Separation of Salts from Xylose at pH 5

A feed stream of sugars from cellulosic biomass was prepared using the procedures, from Example 5 except that the pH of the sugar stream was maintained at pH 5 prior to feeding it to the ion exclusion column.

Concentrations of sulfate were measured by ion exchange chromatography and concentrations of ammonium were measured by colourimetric assay. Total solids were measured as described in Example 5. The results of the elution at pH 5 are shown in FIGS. 5A, 5B and 5C.

Figure 5A:
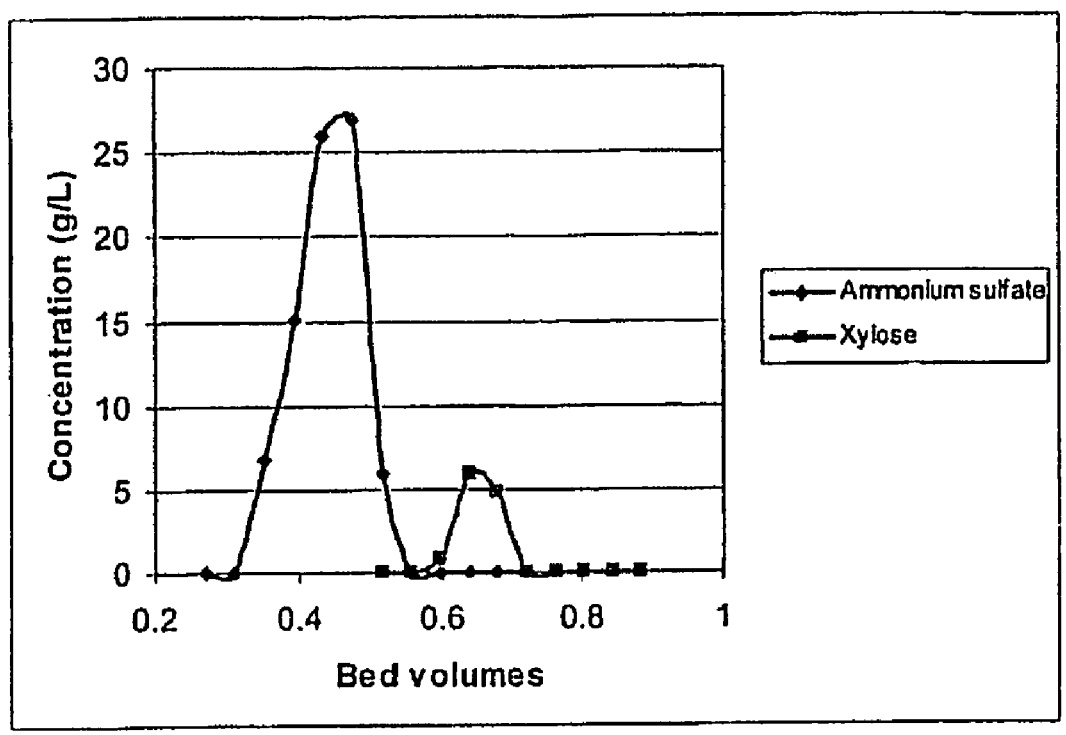
FIG. 5A shows the elution of ammonium sulfate and xylose.

As shown in FIG. 5A, the ammonium sulfate elutes first, followed by the elution of xylose. The separation was good in that there was very little bleeding of salts into the xylose peak with both the ammonium sulfate concentration and the concentration of xylose reaching close to zero between the two peaks.

Figure 5B:
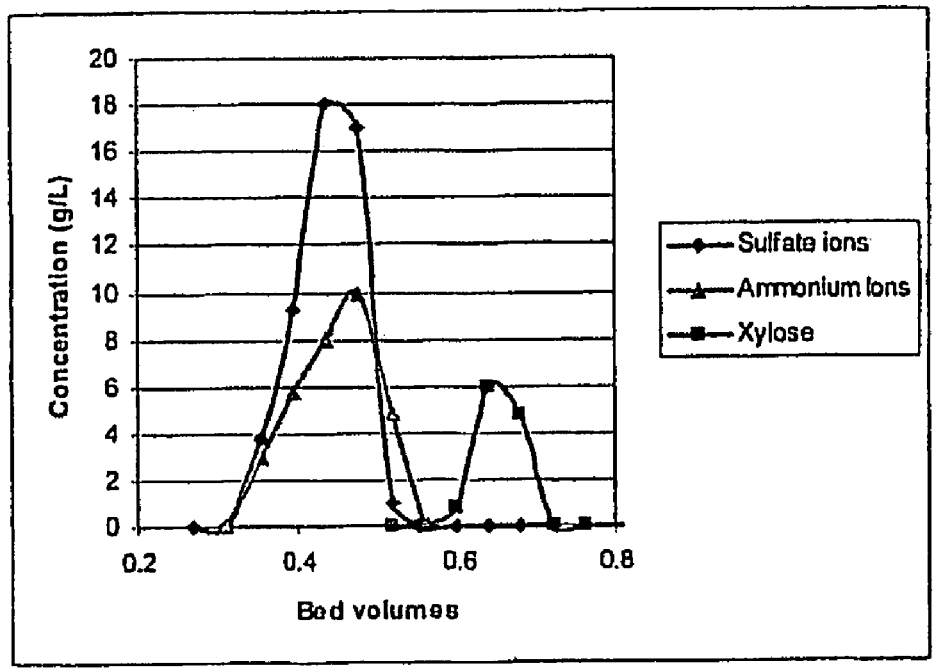
FIG. 5B shows the elution of sulfate ions, ammonium ions and xylose.

FIG. 5B shows the sulfate ion, ammonium ion and xylose content of select pulse test fractions at pH 5. The sulfate and ammonia elution peaks overlapped and were followed by an elution peak containing xylose.

Figure 5C:
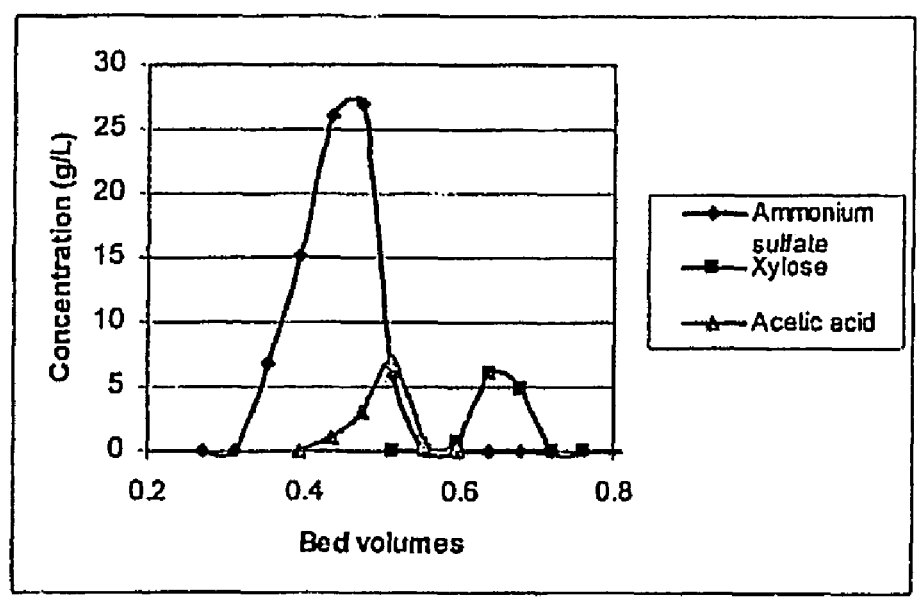
FIG. 5C shows the elution of ammonium sulfate, xylose and acetic acid.

FIG. 5C compares the elution of ammonium sulfate, xylose and acetic acid at pH 5. At this pH, "acetic acid" includes ⅓ acid and ⅔ acetate salts. As can be seen from FIG. 5C, acetic acid eluted at the end of the ammonium sulfate peak, but without bleeding into the xylose peak. The acetic acid removal from the xylose is acceptable. A larger bleeding of acetic acid into the xylose stream would be expected at a lower pH, as was observed at pH 3 in Example 2B.

All citations are hereby incorporated by reference.

The present invention has been described with regard to one or more embodiments. However, it will be apparent to persons skilled in the art that a number of variations and modifications can be made without departing from the scope of the invention as defined in the claims.

The embodiments of the invention in which an exclusive property of privilege is claimed are defined as follows:

1. A process for obtaining a product sugar stream from cellulosic biomass comprising cellulose and hemicellulose, the process comprising:
   a) pretreating the cellulosic biomass at a pH of about 0.4 to about 2.0 by adding one or more than one acid to the cellulosic biomass to hydrolyze a portion of the cellulose and at least a portion of the hemicellulose in the cellulosic biomass to produce a pretreated cellulosic biomass comprising glucose, acetic acid and a sugar monomer selected from the group consisting of xylose, arabinose, mannose, galactose and a combination thereof;
   b) adding one or more than one base to the pretreated cellulosic biomass to adjust the pretreated cellulosic biomass to a pH of about 4.0 to about 6.0, thereby producing a neutralized cellulosic biomass comprising inorganic salt and acetate salt;
   c) hydrolyzing the neutralized cellulosic biomass with cellulase enzymes to produce a crude sugar stream;
   d) separating insoluble residue from the crude sugar stream to produce a clarified sugar stream;
   e) treating the clarified sugar stream by ion exclusion chromatography with a cation exchange resin at a pH from 5.0 to 10.0 to produce one or more than one raffinate stream comprising the inorganic salt and acetate salt and a product sugar stream comprising sugar, wherein the concentration of acetic acid plus acetate salt in the clarified sugar stream fed to the ion exclusion chromatography step is greater than 5 g/L; and
   f) recovering the product sugar stream.

2. The process of claim 1 wherein, the ion exclusion chromatography of step e) is performed at a pH of between 6 and 10.

3. The process of claim 2 further comprising a step of recovering the one or more than one raffinate stream.

4. The process of claim 2 wherein, the ion exclusion chromatography of step e) is carried out using a Simulated Moving Bed (SMB) system or an Improved Simulated Moving Bed (ISMB) system.

5. The process of claim 2 wherein the clarified sugar stream is characterized by having a lignosulfonate content of from about 0 to about 4% of the total solids present in the clarified sugar stream.

6. The process of claim 2 wherein the cellulosic biomass is obtained from a feedstock selected from the group consisting of an agricultural waste, corn stover, wheat straw, barley straw, canola straw, oat straw, rice straw, soybean stover, a grass, switch grass, miscanthus, cord grass, reed canary grass, a forestry residue, aspen wood or sawdust, a sugar residue, bagasse and beet pulp.

7. The process of claim 2 wherein the acid is sulfuric acid and the inorganic salt comprises a sulfate salt.

8. The process of claim 2 wherein the dosage of the cellulase enzymes is about 5 to about 50 IU per gram of cellulose.

9. The process of claim 2 wherein pretreatment is selected from the group consisting of steam explosion and dilute acid prehydrolysis.

10. The process of claim 2 wherein the cellulosic biomass is pressed or leached prior step a.

11. The process of claim 4 wherein the SMB system or ISMB system is operated with 4 to 16 shifts of feed and collection positions per cycle.

12. The process of claim 11 wherein the SMB system or ISMB system is operated with 4 to 12 shifts of feed and collection positions per cycle.

13. The process of claim 3 wherein the recovered raffinate stream is used as a fertilizer.

14. The process of claim 2 wherein, in the step of adding (step b)), the one or more than one base is a soluble base.

15. The process of claim 14 wherein the soluble base is selected from the group consisting of sodium hydroxide, potassium hydroxide, ammonia and ammonium hydroxide.

16. The process of claim 2 wherein, in step d, the insoluble residue is separated from the crude sugar stream by microfiltration, plate and frame filtration, crossflow filtration, pressure filtration, vacuum filtration or centrifugation.

17. The process of claim 2 wherein the ion exclusion chromatography is performed at a pH of between 6.5 and 10.

18. The process of claim 2 wherein the ion exclusion chromatography is performed at a pH of between 6 and 8.

19. The process of claim 2 wherein the clarified sugar stream produced in step d) is concentrated prior to or during step e.

20. The process of claim 2 wherein the product sugar stream produced in step e) is concentrated.

21. The process of claim 2 wherein, in step e, one raffinate stream comprising the inorganic salt and acetate salt is produced.

22. A process for producing ethanol comprising:
   a) obtaining cellulosic biomass comprising cellulose and hemicellulose from a feedstock selected from the group consisting of an agricultural waste, corn stover, wheat straw, barley straw, canola straw, oat straw, rice straw, soybean stover, a grass, switch grass, miscanthus, cord grass, reed canary grass, a forestry residue, aspen wood or sawdust, a sugar residue, bagasse and beet pulp;
   b) pretreating the cellulosic biomass at a pH of about 0.4 to about 2.0 by adding one or more than one acid to the cellulosic biomass to hydrolyze a portion of the cellulose and at least a portion of the hemicellulose in the cellulosic biomass to produce a pretreated cellulosic biomass comprising glucose, acetic acid and a sugar monomer selected from the group consisting of xylose, arabinose, mannose, galactose and a combination thereof;
   c) adding one or more than one base to the pretreated cellulosic biomass to adjust the pretreated cellulosic biomass to a pH of about 4.0 to about 6.0, thereby producing a neutralized cellulosic biomass comprising inorganic salt and acetate salt;
   d) hydrolyzing the neutralized cellulosic biomass with cellulase enzymes to produce a crude sugar stream;
   e) separating insoluble residue from the crude sugar stream to produce a clarified sugar stream;
   f) treating the clarified sugar stream by ion exclusion chromatography with a cation exchange resin at a pH from 5.0 to 10.0 to produce one or more than one raffinate stream comprising the inorganic salt and acetate salt and a product sugar stream comprising sugar, wherein the concentration of acetic acid plus acetate salt in the clarified sugar stream fed to the ion exclusion chromatography step is greater than 5 g/L;
   g) recovering the product sugar stream, and the one or more than one raffinate stream; and
   h) fermenting the sugar in the product sugar stream to ethanol.

23. The process of claim 22 wherein, the ion exclusion chromatography of step e) is performed at a pH of between 6 and 10.

24. The process of claim 23 wherein, in step d, the dosage of cellulase enzymes is about 5 to about 50 IU per gram of cellulose.

25. The process of claim 23 wherein, in step b, pretreatment is selected from the group consisting of steam explosion and dilute acid prehydrolysis.

26. The process of claim 23 wherein the acid is sulfuric acid and the inorganic salt comprises a sulfate salt.

27. The process of claim 23 wherein, in step e, the insoluble residue is separated from the crude sugar stream by microfiltration, plate and frame filtration, crossflow filtration, pressure filtration, vacuum filtration or centrifugation.

28. The process of claim 23 wherein, in the step of pretreating (step b)), the clarified sugar stream is characterized by having a lignosulfonate content of from about 0 to about 4% of the total dry solids present in the clarified sugar stream.

29. The process of claim 23 wherein, prior to the step of pretreating (step b)), the cellulosic biomass is pressed or leached.

30. The process of claim 23 wherein, the ion exclusion chromatography of step f) is carried out using a Simulated Moving Bed (SMB) system or an Improved Simulated Moving Bed (ISMB) system.

31. The process of claim 30 wherein the SMB system or the ISMB system is operated with 4 to 16 shifts of feed and collection positions per cycle.

32. The process of claim 31 wherein the SMB system or the ISMB system is operated with 4 to 12 shifts of feed and collection positions per cycle.

33. The process of claim 23 wherein, the recovered raffinate stream is used as a fertilizer.

34. The process of claim 23 wherein, in the step of adding (step c)), the one or more than one base is a soluble base.

35. The process of claim 34 wherein the soluble base is selected from the group consisting of sodium hydroxide, potassium hydroxide, ammonia and ammonium hydroxide.

36. The process of claim 23 wherein, the ion exclusion chromatography of step f) is performed at a pH of between 6 and 8.

37. The process of claim 23 wherein, the ion exclusion chromatography of step f) is performed at a pH of between 6.5 and 10.

38. The process of claim 23 wherein the clarified sugar stream produced in step e) is concentrated prior to or during step f).

39. The process of claim 23 wherein the product sugar stream produced in step f) is concentrated.

40. The process of claim 23 wherein, in step f), one raffinate stream comprising the inorganic salt and acetate salt is produced.

41. A process for obtaining a product sugar stream from a crude sugar stream, the crude sugar stream produced from conversion of cellulosic biomass to sugar, the process comprising:
   a) separating insoluble residue from the crude sugar stream to produce a clarified sugar stream;
   b) treating the clarified sugar stream by ion exclusion chromatography with a cation exchange resin at a pH from 5.0 to 10.0 to produce one or more than one raffinate stream comprising sulfate and acetate salts, and a product stream comprising sugar, wherein the concentration of acetic acid plus acetate salt in the clarified sugar stream fed to the ion exclusion chromatography step is greater than 5 g/L; and
   c) obtaining the product sugar stream.

42. The process of claim 41 wherein, during step c), the one or more than one raffinate stream is recovered.

43. The process of claim 41 wherein, the ion exclusion chromatography of step b) is carried out using a Simulated Moving Bed (SMB) system or an Improved Simulated Moving Bed (ISMB) system.

44. The process of claim 41 wherein, the ion exclusion chromatography of step b) is performed at a pH of between 6 and 10.

45. A process for obtaining one or more than one raffinate stream enriched in inorganic salt and acetate salt, the process comprising:
   a) obtaining a clarified stream comprising sugar, inorganic salt and at least one of an acetate salt and acetic acid originating from a previous hydrolysis of the cellulosic biomass; and
   b) treating the clarified stream by ion exclusion chromatography with a cation exchange resin at a pH from 5.0 to 10.0 to produce the one or more than one raffinate stream enriched in inorganic salt and acetate salt, and a stream comprising sugar, wherein the concentration of acetic acid plus acetate salt in the clarified stream fed to the ion exclusion chromatography step is greater than 5 g/L.

46. The process of claim 45, wherein the clarified stream comprising sugar is a still bottoms stream resulting from the steps of (i) fermentation of a sugar stream resulting from hydrolysis of the cellulosic biomass, said fermentation resulting in a fermentation broth comprising ethanol; and (ii) distillation of the fermentation broth to produce concentrated ethanol and the still bottoms stream, wherein insoluble residue is removed in a solid-liquid separation step conducted prior to step b.

47. The process of claim 46, wherein the insoluble residue is removed prior to the step of fermentation (step i)).

48. The process of claim 46, wherein insoluble residue is removed from the still bottoms stream.

* * * * *

UNITED STATES PATENT AND TRADEMARK OFFICE
CERTIFICATE OF CORRECTION

| | | |
|---|---|---|
| PATENT NO. | : 8,003,352 B2 | Page 1 of 3 |
| APPLICATION NO. | : 11/658338 | |
| DATED | : August 23, 2011 | |
| INVENTOR(S) | : Brian Foody et al. | |

It is certified that error appears in the above-identified patent and that said Letters Patent is hereby corrected as shown below:

ON THE TITLE PAGE ITEM [56] FOREIGN PATENT DOCUMENT:

Foreign Patent Document, "WO WO2006007691 A1* 1/2006" should read --WO WO2006/007691 A1* 1/2006--.

COLUMN 1:

Line 25, "feedstocks" should read --feedstocks.--; and
Line 26, "from," should read --from--.

COLUMN 2:

Line 36, "art" should read --prior art methods for--; and
Line 37, "high;" should read --high--.

COLUMN 3:

Line 36, "over," should read --over--.

COLUMN 4:

Line 39, "tractions" should read --fractions--; and
Line 40, "are" should read --is--.

COLUMN 5:

Line 5, "are" should read --is--;
Line 20, "are" should read --is--;
Line 49, "are" should read --is--; and Signed and Sealed this
Twenty-second Day of November, 2011

David J. Kappos
*Director of the United States Patent and Trademark Office*

Line 50, "colour." should read --color.--.

COLUMN 6:

Line 1, "during;" should read --during--; and
Line 14, "men" should read --then--.

COLUMN 7:

Line 28, "1.0." should read --10.--.

COLUMN 8:

Line 53, "die" should read --the--; and
Line 56, "selected," should read --selected--.

COLUMN 9:

Line 32, "man" should read --than--.

COLUMN 10:

Line 31, "in," should read --in--.

COLUMN 11:

Line 60, "with," should read --with--.

COLUMN 13:

Line 2, "crude," should read --crude--;
Line 41, "presents" should read --present,--; and
Line 56, "terra" should read --term--.

COLUMN 17:

Line 20, "12 O'clock." should read --12 o'clock.--;
Line 22, "9 O'clock." should read --9 o'clock.--;
Line 23, "O'clock" should read --o'clock--;
Line 30, "3 O'clock." should read --3 o'clock.--;
Line 31, "12 O'clock." should read --12 o'clock.--;
Line 34, "die" should read --the--;
Line 37, "1 O'clock," should read --1 o'clock,--; and "4 O'clock." should read
--4 o'clock,--; and

CERTIFICATE OF CORRECTION (continued)
U.S. Pat. No. 8,003,352 B2

Line 38, "7 O'clock," should read --7 o'clock,--; and "10 O'clock," should read --10 o'clock,--.

COLUMN 18:

Line 10, "in," should read --in--.

COLUMN 20:

Line 10, "hot" should read --not--.

COLUMN 21:

Line 25, "case-even" should read --case even--; and
    Line 67, "provide" should read --provided--.

COLUMN 22:

Line 29, "subjecting," should read --subjecting--;
    Line 61, "were" should read --was--; and
    Line 62, "1 nil" should read --1 ml--.

COLUMN 23:

Line 18, "procedures," should read --procedures--; and
    Line 23, "colourimetric" should read --colorimetric--.

COLUMN 24:

Line 16, "wherein," should read --, wherein--;
    Line 22, "wherein," should read --, wherein--; and
    Line 46, "prior" should read --prior to--.

COLUMN 25:

Line 49, "wherein," should read --, wherein--.

COLUMN 26:

Line 4, "wherein," should read --, wherein--;
    Line 14, "wherein," should read --, wherein--;
    Line 21, "wherein," should read --, wherein--;
    Line 24, "wherein," should read --, wherein--;
    Line 52, "wherein," should read --, wherein--; and
    Line 56, "wherein," should read --, wherein--.